(12) United States Patent  
Brekke et al.

(10) Patent No.: US 10,080,941 B2  
(45) Date of Patent: Sep. 25, 2018

(54) METHOD, SYSTEM, AND APPARATUS FOR ANALYZING A SPORTING APPARATUS

(71) Applicant: Dunlop Sports Company Limited, Kobe (JP)

(72) Inventors: Dustin J. Brekke, Fountain Valley, CA (US); Jay Vogler, Huntington Beach, CA (US); Patrick Ripp, Seal Beach, CA (US); Mitchell Samson, Newport Beach, CA (US); Jeff D. Brunski, Los Angeles, CA (US); Brian D. Schielke, Los Angeles, CA (US); Scott A. Carlyle, Costa Mesa, CA (US); Phillip C. Seagram, Long Beach, CA (US); Christopher J. Beck, Costa Mesa, CA (US); Eli Miller, Costa Mesa, CA (US); Kirk D. Bacon, Long Beach, CA (US)

(73) Assignee: SUMITOMO RUBBER INDUSTRIES, LTD., Hyogo (JP)

( * ) Notice: Subject to any disclaimer, the term of this patent is extended or adjusted under 35 U.S.C. 154(b) by 49 days.

(21) Appl. No.: 14/848,083

(22) Filed: Sep. 8, 2015

(65) Prior Publication Data
US 2017/0001072 A1   Jan. 5, 2017

Related U.S. Application Data

(60) Provisional application No. 62/188,393, filed on Jul. 2, 2015.

(51) Int. Cl.
*A63B 69/36* (2006.01)
*A63B 60/46* (2015.01)
(Continued)

(52) U.S. Cl.
CPC .......... *A63B 60/46* (2015.10); *A63B 71/0622* (2013.01); *G01S 19/19* (2013.01);
(Continued)

(58) Field of Classification Search
USPC ................................. 473/219, 221–224, 409
See application file for complete search history.

(56) References Cited

U.S. PATENT DOCUMENTS 5,441,256 A * 8/1995 Hackman ............... A63B 53/00
                                                              473/233
7,021,140 B2   4/2006 Perkins
(Continued)

OTHER PUBLICATIONS http://www.zepp.com/golf/club-sensor-setup/ Zepp Golf Swing Analysis and Trainer System. Zepp USA, Inc. 2015.

*Primary Examiner* — Nini Legesse
(74) *Attorney, Agent, or Firm* — Stetina Brunda Garred and Brucker; Mark B. Garred

(57) ABSTRACT

The present application is direction to a computing device having a memory and a processor. The processor is configured to receive data generated in response to a motion of a sporting apparatus, where the data includes a first data relating to a first characteristic of the motion of the sporting apparatus. The first data is based on a comparison between at least two different directional segments of a path created by a first location on the sporting apparatus during the motion of the sporting apparatus. The processor is further configured to analyze the data to determine a skill value, determine a recommended sporting apparatus from a group of at least two sporting apparatuses based on the skill value; and transmit information relating to the recommended sporting apparatus.

13 Claims, 10 Drawing Sheets

(51) Int. Cl.
*A63B 71/06* (2006.01)
*G01S 19/19* (2010.01)
*G06F 19/00* (2018.01)
*G06K 9/00* (2006.01)
*A63B 102/32* (2015.01)
*A63B 102/06* (2015.01)
*A63B 102/16* (2015.01)
*A63B 102/02* (2015.01)
*A63B 102/14* (2015.01)

(52) U.S. Cl.
CPC ..... *G06F 19/3481* (2013.01); *G06K 9/00342* (2013.01); *G06K 9/00523* (2013.01); *A63B 2071/0647* (2013.01); *A63B 2071/0658* (2013.01); *A63B 2102/02* (2015.10); *A63B 2102/06* (2015.10); *A63B 2102/065* (2015.10); *A63B 2102/14* (2015.10); *A63B 2102/16* (2015.10); *A63B 2102/32* (2015.10); *A63B 2220/13* (2013.01); *A63B 2220/16* (2013.01); *A63B 2220/34* (2013.01); *A63B 2220/44* (2013.01); *A63B 2225/20* (2013.01); *A63B 2225/50* (2013.01); *A63B 2225/54* (2013.01)

(56) References Cited

U.S. PATENT DOCUMENTS

| | | | |
|---|---|---|---|
| 7,024,351 B2 | 4/2006 | Wang | |
| 7,234,351 B2 | 6/2007 | Perkins | |
| 7,766,757 B2 | 8/2010 | Brooks et al. | |
| 8,257,191 B2* | 9/2012 | Stites | A63B 69/36 473/131 |
| 8,337,335 B2* | 12/2012 | Dugan | A63B 69/3623 473/212 |
| 8,587,114 B2 | 10/2013 | Papadourakis | |
| 8,672,779 B1* | 3/2014 | Sakyo | A63B 24/0006 473/223 |
| 8,696,482 B1* | 4/2014 | Pedenko | A63B 69/3632 473/221 |
| 8,715,096 B2 | 5/2014 | Cherbini | |
| 8,781,610 B2 | 7/2014 | Han | |
| 8,956,238 B2* | 2/2015 | Boyd | A63B 24/0003 473/223 |
| 8,979,665 B1* | 3/2015 | Najafi | G09B 19/0038 473/266 |
| 8,989,441 B2 | 3/2015 | Han et al. | |
| 9,339,714 B2* | 5/2016 | Syed | A63B 24/0003 |
| 2002/0077189 A1 | 6/2002 | Tuer | |
| 2003/0207718 A1 | 11/2003 | Perlmutter | |
| 2007/0111811 A1* | 5/2007 | Grober | A63B 69/3638 473/131 |
| 2007/0270214 A1* | 11/2007 | Bentley | A61B 5/1122 463/30 |
| 2010/0151956 A1* | 6/2010 | Swartz | A63B 24/0006 473/199 |
| 2012/0277017 A1* | 11/2012 | Boyd | A63B 24/0003 473/223 |
| 2012/0289354 A1* | 11/2012 | Cottam | A63B 69/3658 473/223 |
| 2012/0295726 A1 | 11/2012 | Cherbini | |
| 2013/0260909 A1* | 10/2013 | Margoles | A63B 69/3623 473/223 |
| 2013/0267335 A1* | 10/2013 | Boyd | A63B 69/36 473/222 |
| 2013/0288829 A1* | 10/2013 | Kimizuka | A63B 53/00 473/409 |
| 2013/0344973 A1* | 12/2013 | Margoles | A63B 69/3623 473/223 |
| 2014/0051526 A1* | 2/2014 | Johnson | A63B 24/0003 473/238 |
| 2014/0179454 A1* | 6/2014 | Worobets | G06F 17/40 473/223 |
| 2015/0018130 A1* | 1/2015 | Johnson | G06K 9/00342 473/409 |

* cited by examiner

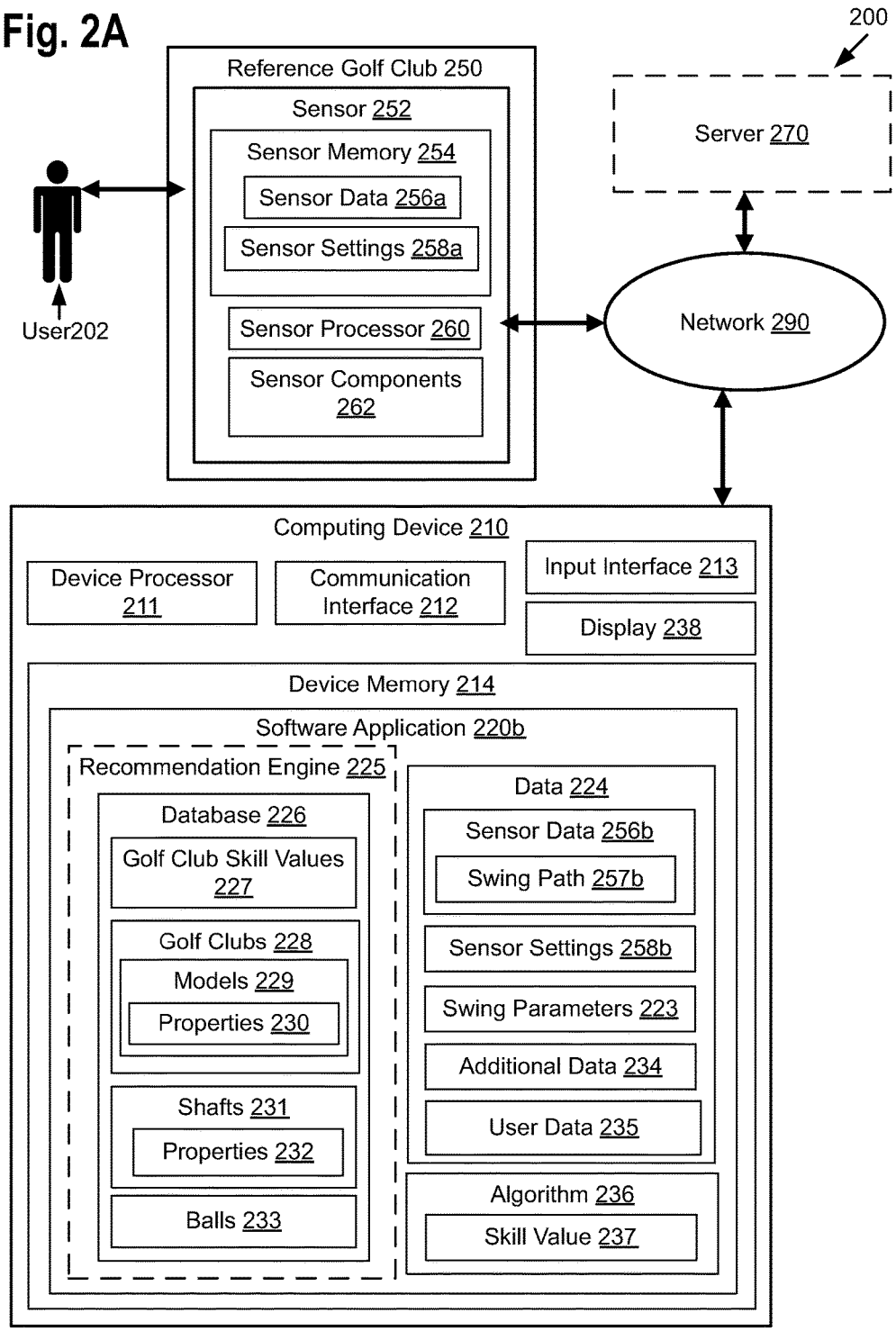

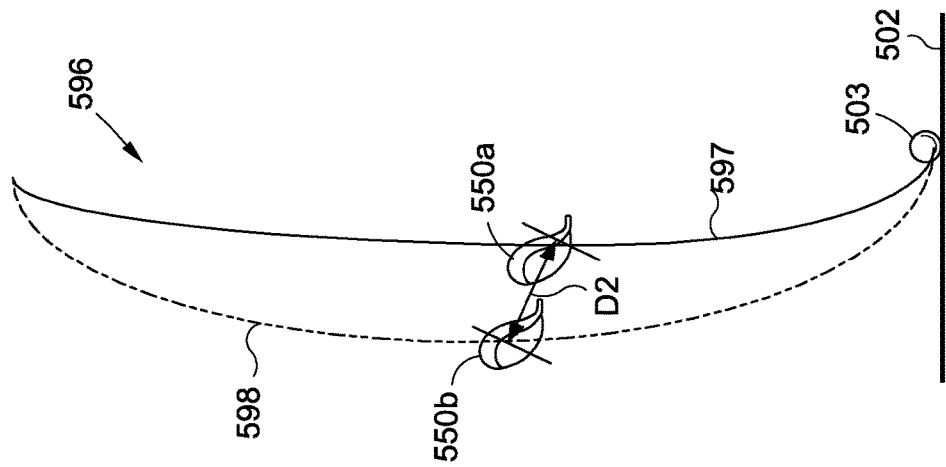
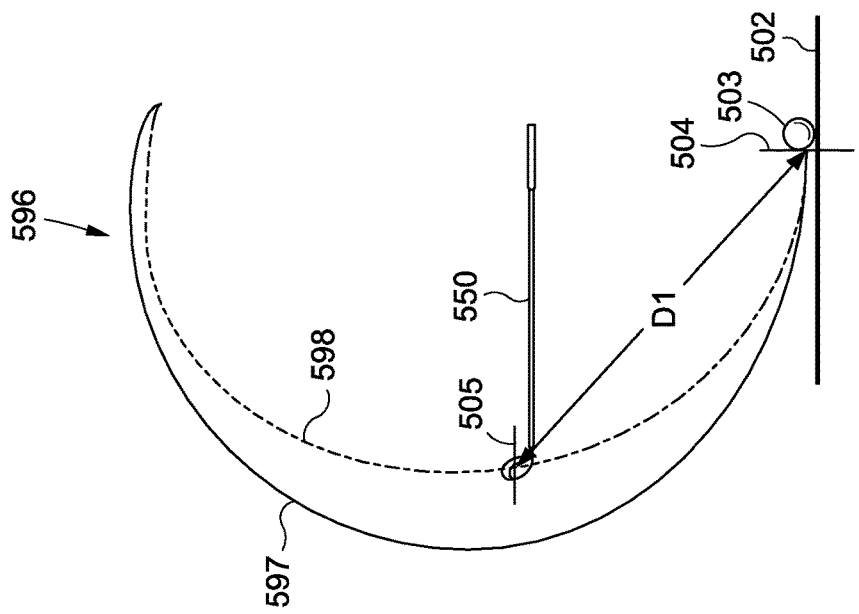

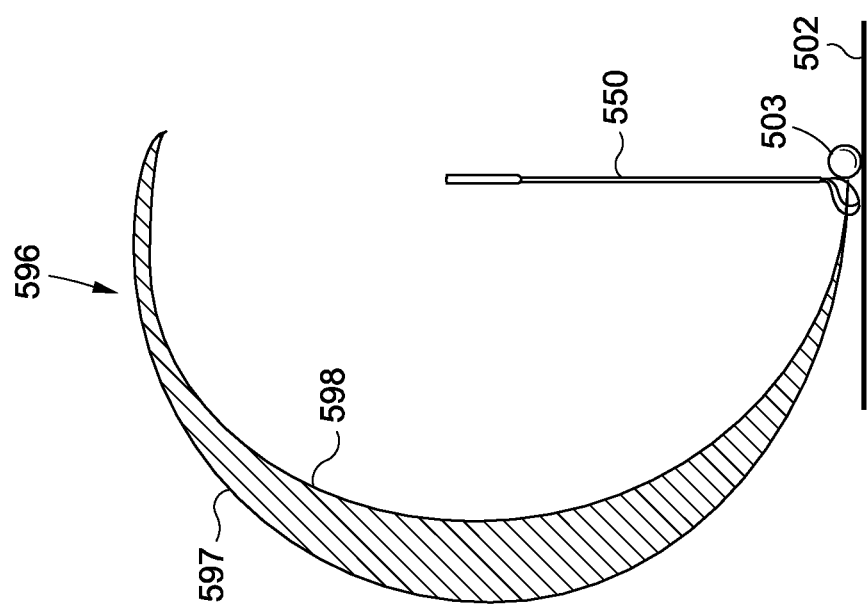

METHOD, SYSTEM, AND APPARATUS FOR ANALYZING A SPORTING APPARATUS

BACKGROUND

Golf club fitting has been around since the early stages of the golf game. Early systems utilized manual measurements of golf clubs and players to determine the proper fit for each player. However, with the need for more advanced and accurate fitting methods and systems, sports enthusiasts have turned to technical innovations in an effort to improve their game, including the use of monitoring devices used to determine and display information specific to the enthusiast, such as a golfer's swing path. Golfers and golf club equipment manufacturers have been increasingly relying upon sensors and monitors to evaluate a golfer's swing. Sensors and monitors may track conditions, such as club head speed, attack angle, launch angle, golf ball spin rate and spin direction, and so on. And sellers of golf club equipment, including outlets that specialize in golf club fitting, increasingly rely on such sensors and monitors to assist a prospective purchaser in selecting golf clubs that best match their particular golf swing characteristics.

One such monitoring device that is commercially available is the "SB2" sensor, available from Swingbyte, LLC (previously Swingbyte, Inc.) of Chicago, Ill. Such sensors, as described in U.S. Pat. No. 8,696,482, incorporated herein by reference, are typically removeably attached to the shaft of a golf club, for example with a clamping mechanism, or fixed to the shaft, for example, with an adhesive. As is now known by virtue of co-pending U.S. patent application Ser. No. 14/564,933, filed Dec. 9, 2015, assigned to the assignee of the present application, hereby incorporated by reference, monitoring devices may also be placed within sporting apparatus, such as the head, shaft, and/or grip of golf clubs.

Such monitoring devices capture and analyze golf swing (or other sporting apparatus motion) data by attaching the monitoring device to a golf club either below the grip or on the cap, or by integrating the sensor into the shaft or head. After hitting a shot or swinging the golf club (or other sporting apparatus), players and instructors can view an interactive, three-dimensional animation of the swing, along with key metrics, such as club head speed, path, plane, and various angles at impact. Such monitoring devices may use a transmitter to send processed linear and angular movement data that defines a sporting apparatus swing, e.g., a golf club swing, to a receiver on a mobile device, such as a smart phone, tablet computer, or laptop computer. A computer application running on the mobile device may receive the processed data, process the data further and display a graphical representation of the entire swing with comprehensive statistics associated with the swing.

Yet, even with the implementation of sensors such as those discussed above, and the wide use of digital measurements in fitting golf clubs, fitting methods that utilize parameters of the swing of the golfer as measured by a sensor attached to a golf club have yet to be widely accepted and implemented.

SUMMARY

The following presents a general summary of aspects of the disclosure in order to provide a basic understanding thereof. This summary is not an extensive overview of the disclosure. It is not intended to identify key or critical elements of the disclosure or to delineate the scope of the disclosure. The following summary merely presents some concepts of the disclosure in a general form as a prelude to the more detailed description provided below.

In one implementation of the present disclosure, a computing device is disclosed comprising: a computer readable memory configured to store instructions; and a processor configured to execute the instructions to: receive data generated in response to a motion of a sporting apparatus, the data including a first data relating to a first characteristic of the motion of the sporting apparatus; analyze the data to determine a skill value; determine a recommended sporting apparatus from a group of at least two sporting apparatuses based on the skill value; and transmit information relating to the recommended sporting apparatus, wherein the first data is based on a comparison between at least two different directional segments of a path created by a first location on the sporting apparatus during the motion of the sporting apparatus.

In another implementation, a computing device is disclosed comprising: a display; a computer readable memory configured to store instructions; and a processor configured to execute the instructions to: receive data generated in response to a motion of a sporting apparatus, the data including a first data relating to a first characteristic of the motion of the sporting apparatus, the first characteristic including a first attribute of a backswing of a swing path of a location on the sporting apparatus and a second attribute of a downswing segment of the swing path of the location on the sporting apparatus; analyze the data to determine a skill value by comparing the first attribute and the second attribute; and transmit the skill value to the display.

In yet another implementation, a method for determining a recommended sporting apparatus is disclosed, the method comprising: receiving data generated in response to a motion of a sporting apparatus, the data including a first data relating to a first characteristic of the motion of the sporting apparatus, the first characteristic including a first attribute of a first directional segment of a swing path of a location on the sporting apparatus and a second attribute of a directional segment of the swing path created by the first location on the sporting apparatus; analyzing the data to determine a skill value by comparing the first attribute and the second attribute; determining a recommended sporting apparatus from a group of at least two sporting apparatuses based on the skill value; and transmitting information relating to the recommended sporting apparatus.

In another implementation of the present disclosure, a system is disclosed, the system comprising: a reference golf club; a sensor engaged with the reference golf club; and a computing device, the computing device comprising: a computer readable memory configured to store instructions; and a processor configured to execute the instructions to: receive data generated by the sensor in response to a motion of the reference golf club, the data including a first data relating to a first characteristic of the motion of the reference golf club, the first characteristic based on at least two different directional segments of a swing path created by a first location on the reference golf club during the motion of the reference golf club; analyze the data to determine a skill value; determine a recommended golf club from a group of at least two golf clubs based on the skill value; and transmit information relating to the recommended golf club.

BRIEF DESCRIPTION OF THE DRAWINGS

The present disclosure is illustrated by way of example and not limited in the accompanying figures, in which like reference numerals indicate similar elements throughout, and in which:

FIG. 2A is an illustration of a system for analyzing a sporting apparatus, according to one implementation of the present disclosure.

FIGS. 5A-5E illustrate various representations of swing parameters associated with a golf club swing, according to one implementation of the present disclosure.

DETAILED DESCRIPTION

Figure 1:
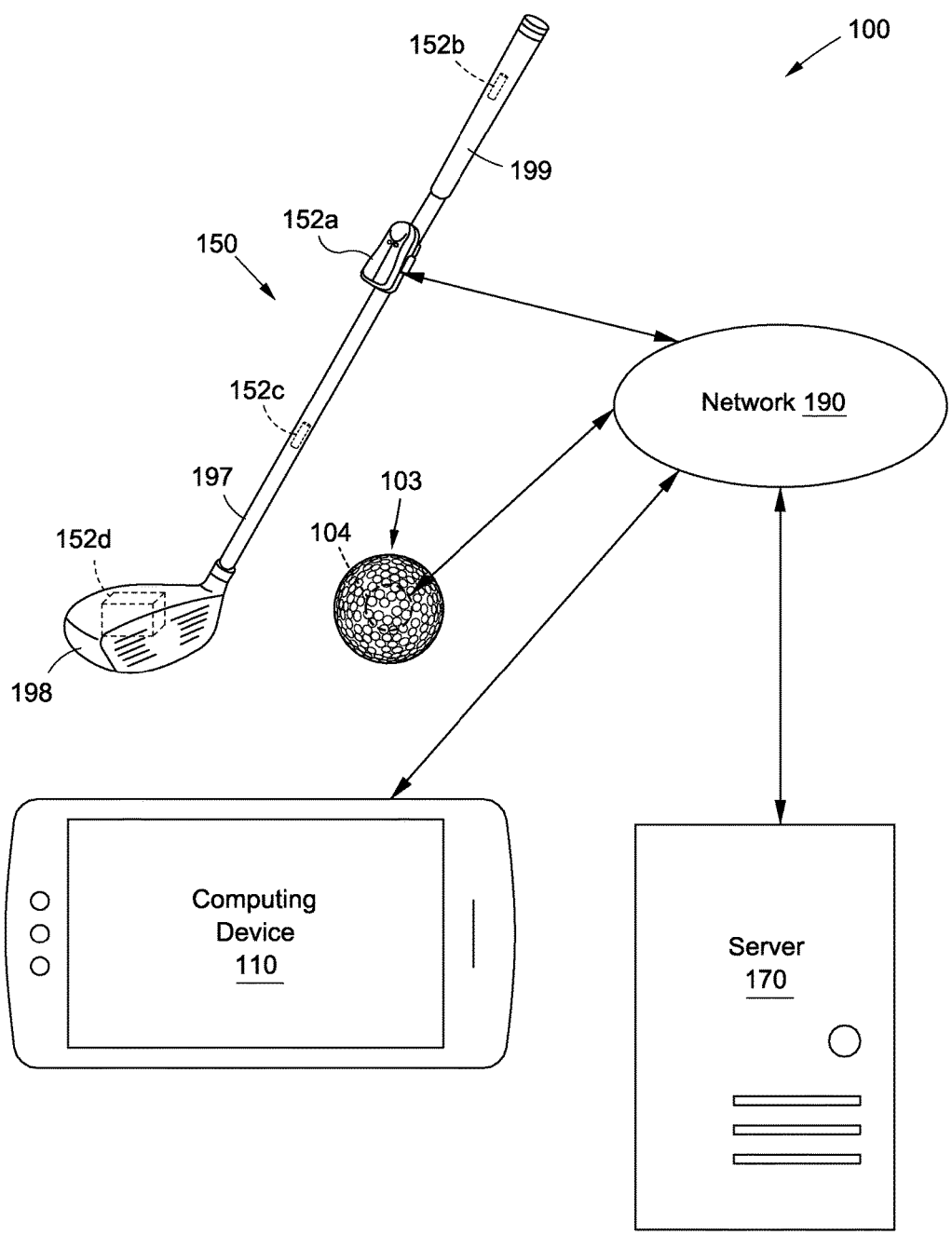
FIG. 1 is an illustration of a system for analyzing a sporting apparatus, according to one implementation of the present disclosure.

It should be noted that for simplicity and clarity the specification is directed toward the use of golf clubs, such as reference golf club 150 of FIG. 1, for example. However, the specification is not intended to be limited to only implementations including golf clubs. As such, the use of the term golf club (and implementations thereof) throughout the specification is intended to include substitution with any suitable sporting apparatus (and like implementations thereof), including baseball bats, softball bats, cricket bats, hockey sticks, tennis rackets, squash rackets, racquetball rackets, badminton rackets, lacrosse sticks, a boxing glove, and further includes sports apparel, and devices such as video game controllers intended to mimic such sporting apparatus. In addition, sporting apparatuses that may impact or be associated with an impact with a device are also included within suitable sporting apparatuses that may be used in lieu of a golf club in the specification. For example, a shoe configured to kick a soccer ball or football, or apparel, such as a golf glove, body suit, watch, or helmet, that a user might wear when causing an impact, are all included within the term sporting apparatus.

Referring to FIG. 1, FIG. 1 is an illustration of a system for analyzing a sporting apparatus, according to one implementation of the present disclosure. FIG. 1 includes reference golf club 150, golf ball 103, sensor 152a, sensor 152b, sensor 152c, and sensor 152d, (hereinafter referred to collectively as sensors 152), network 190, server 170, and computing device 110. Reference golf club 150 includes golf club head 198, golf club grip 199, and golf club shaft 197. The golf ball 103 includes ball sensor 104. Each of the sensors 152, network 190, server 170, reference golf club 150, and computing device 110 will described in more detail with reference to FIG. 2A-FIG. 7.

The reference golf club 150 includes any type of golf club, including a driver, an iron, a wedge, or a putter, for example. Preferably, reference golf club 150 includes the type of golf club being analyzed by a system 100. For example, if a user of the reference golf club 150 is utilizing the system 100 to analyze his/her swing during use of a driver, then reference golf club 150 is preferably also a driver in order to generate more accurate results.

The network 190 enables communication between sensors 152, computing device 110, and server 170. Although network 190 is illustrated as being a single network, the illustration of FIG. 1 is not intended to limit the scope of the disclosure. As such, the network 190 may include any number of networks in communication with each other, and/or any number of separate networks not in communication.

The computing device 110 is configured to receive and/or transmit data over the network 190 from and/or to sensors 152 and/or server 170. The computing device 110 may be a desktop computer, a laptop computer, a tablet computer, a mobile device, a wearable device, such as a watch, or any other suitable device capable of receiving and/or transmitting data and operating a software program, for example, as described in U.S. application Ser. No. 14/694,568, filed Apr. 23, 2015, assigned to the assignee of the present application, and incorporated in its entirety by reference herein. Although the computing device 110 is illustrated as being a single computing device, the illustration of FIG. 1 is not meant to limit the scope of the disclosure. In some implementations, there may be any number of computing devices in communication with each other and/or the network 190.

The server 170 is configured to receive and/or transmit data over the network 190 from and/or to the sensors 152 and/or the computing device 110. Although the server 170 is illustrated as being a single server, the illustration of FIG. 1 is not meant to limit the scope of the disclosure. Thus, the server 170 may include any number of servers in communication with each other and/or the network 190.

The sensors 152 are configured to generate and record data relating to characteristics of motion of the reference golf club 150 during a motion of the reference golf club 150, such as a full swing including a backswing and a downswing of the reference golf club 150. The sensors 152 may be attached externally, to the shaft 197, for example, such as sensor 152a, embedded within the shaft 197, such as sensor 152c, embedded within the grip 199 portion of the shaft 197, such as sensor 152b, or embedded within the club head 198, such as sensor 152d, for example, as illustrated and described in U.S. application Ser. No. 14/488,140, filed Sep. 16, 2014, assigned to the applicant of the present application, and incorporated in its entirety by reference herein. Although four different locations for the sensors 152 are illustrated in FIG. 1, the specification is not intended to be limited to the illustrations of FIG. 1. For example, the sensors 152 may be embedded within, or attached to, the golf club 150 at any location. In addition, any number of sensors 152 may be included in and/or on the golf club 150. For example, in some implementations, only one of the sensors 152 may be utilized, while in other implementations, multiple sensors 152 may be utilized to generate data at different locations on the golf club 150.

The sensors 152 may each include a dedicated housing for protecting the components of the sensors 152, or alternatively, the sensors 152 may utilize the interior walls or surface(s) of the reference golf club 150 as a housing.

The sensors 152 may be attached to or inserted within the shaft and/or the club head of the reference golf club 250 using clamping mechanisms, adhesive, plugs, mechanical fasteners, or another suitable method capable of holding the sensors 152 in place during a full swing of the reference golf club 150.

The ball sensor 104 may function similarly to the sensors 152 except for the ball sensor 104 is located within the golf ball 103. The ball sensor 104 therefore may measure impact conditions such as launch angle, spin rates, deformation, and other data relating to the golf ball 103. In addition, the ball sensor 104 may measure the distance the golf ball 103 travels after impact, including carry distance and roll distance, and may also track the location of the ball on the course, using GPS, for example. The ball sensor 104 may transmit the data collected over the network 190, and may include similar circuitry and components as the sensors 152, which will be described in greater detail with reference to the sensor 252 in FIG. 2A and FIG. 2B.

Now referring to FIG. 2A, FIG. 2A is an illustration of a system for analyzing a sporting apparatus, according to one implementation of the present disclosure. System 200 of FIG. 2A includes user 202, reference golf club 250, sensor 252, server 270, network 290, and computing device 210. The sensor 252 includes the sensor memory 254 configured to store sensor data 256a and sensor settings 258a, sensor processor 260, and sensor components 262. The computing device 210 includes device processor 211, communication interface 212, input interface 213, display 238, and device memory 214. The device memory 214 is configured to store software application 220b which includes recommendation engine 225, data 224, and algorithm 236. The recommendation engine 225 includes database 226 which includes golf club skill values 227, golf clubs information 228 which includes identification of model 228, properties 230, and component information, including for shafts 231 which includes properties 232, and balls 233. The data 224 includes sensor data 256b which includes swing path 257b, sensor settings 258b, swing parameters 223, additional data 234, and user data 235. The algorithm 236 includes skill value 237.

It should be noted that the reference golf club 250, the sensor 252, the server 270, the network 290, and the computing device 210 correspond respectively to the reference golf club 150, the sensors 152, the server 170, the network 190, and the computing device 110 of FIG. 1.

System 200 includes network 290 that is configured to allow communication between the sensor 252, the server 270, the computing device 210, and any other devices in communication with the network 290. The network 290 may include any medium that facilitates transfer of a program code from one place to another, including, for example, implementations where the software is transmitted from the server 270, a web site, the computing device 210, the sensor 252, or another remote source. The network 290 may utilize coaxial cable, fiber optic cable, twisted pair, digital subscriber line (DSL), or wireless technologies such as infrared, radio, which includes Bluetooth™ and ZigBee™, and microwave. The network 290 may be a local area network (LAN) or a wide area network (WAN). When system 200 is used in a LAN networking environment, the computing device 210, the server 270, and the sensor 252 are connected to the LAN through a network interface or adapter. When used in a WAN networking environment, the computing device 210, the server 270, and the sensor 252 may include a modem or other means for establishing communications over the WAN, such as the Internet.

In some implementations, the network 290 may be connected to any number of the sensors 252 such that the server 270 and/or the computing device 210 receive the data 224 from each of the sensors 252. As a result, the software application 220b can be dynamically updated using new information from each of the sensors 252, i.e., has the capability of learning. For example, the recommended golf clubs 228, shafts 231, and balls 233 may be compared to real-life or digital data, i.e., validation data, that either validate or invalidate the results of the recommendation engine 225. In such an example, if the golf club recommended actually does not provide the user 202 with the most carry distance, for example, this information (i.e., an indication of an incorrect recommendation) can be input back into the database 226 to dynamically update the associated golf club skill values 227 and/or swing parameters 223 associated with the recommended golf club to match the skill value 237 and/or swing parameters 223 of the user 202 during the swing of the reference golf club 250. As a result, the feedback can be used to dynamically update the algorithm 236 such that more accurate recommendations are made by the recommendation engine 225.

The system 200 further includes the server 270 which will be described in further detail below with reference to FIG. 2B. It should be noted that the server 270 is illustrated with dashed lines to indicate that the server 270 may not be necessary in all implementations. For example, in implementations where the computing device 210 is capable of handling the data storage requirements of the software application 220b, the server 270 may not be necessary.

The system 200 further includes the sensor 252 configured to record sensor data 256a before, during, and after a motion of the reference golf club 250. The sensor 252 is configured to be capable of recording three dimensional motion of the reference golf club 250. The sensor 252 may be a sensor similar to that of the Swingbyte "SB2" sensor described above, or may be any sensor capable of recording the motion of the reference golf club 250. In addition, the sensor 252 may be located in a golf ball, such as the sensor 104 in the golf ball 103 of FIG. 1.

The sensor 252 includes the sensor memory 254 and the sensor processor 260. The sensor processor 260 is configured to execute computer-readable instructions that are stored in the sensor memory 254. The instructions may be, for instance, instructions for gathering sensor data 256a according to the sensor settings 258a, and may further include instructions for utilizing the sensor components 262, including, for example, a three-axis accelerometer, a three-axis gyroscope, and a magnometer. The sensor processor 260 may access the sensor memory 254 by way of a system bus, for example. The sensor 252 also includes a communication interface, similar to that of the communication interface 212 of the computing device 210, configured to allow external devices, such as the server 270 and the computing device 210, to communicate with the sensor 252 and also allow the sensor 252 to communicate with the external devices. For example, in some implementations, the sensor 252 may receive instructions for execution by the sensor processor 260 from an external device.

Various functions of the sensor memory 254 may be implemented in hardware, software, or any combination thereof. If implemented in software, the functions may be stored as one or more instructions or code and transmitted over a computer-readable medium. A computer-readable storage media may include any available storage media that can be accessed by a computer, and more specifically by a processor, such as the sensor processor 260. By way of example, and without limitation, computer-readable storage media can comprise RAM, ROM, EEPROM, CD-ROM, or other optical disk storage, magnetic disk storage or other magnetic storage devices, or any other medium that can be used to carry or store desired program code in the form of instructions or data structures that can be accessed by a computer, e.g., sensor processor 260. In some implementations, the sensor 152 may use a flash memory to store the data and instructions.

The sensor components 262 may include a battery, and a battery charging connection, such as a USB or mini-USB port, for example. The sensor components 262 may further include a Global Positioning System (GPS) device, a clock, and other suitable devices necessary to capture the sensor data 256a needed for system 200. For example, the GPS device within the sensor 252 may be used to assist in tracking the weather conditions, turf conditions, altitude conditions, or other information that may factor into the motion-gathered sensor data 256a of the reference golf club 250.

The sensor components 262 may include a circuit board onto which one or more subcomponents, such as microprocessors, transmitters, accelerometers, resistors, capacitors, etc., may be mounted, arranged and connected.

The sensor components 262 may further include a three-axis accelerometer. The accelerometer measures the proper acceleration of the reference golf club 250 during a motion of the reference golf club 250. Due to the three-axis measurements, the accelerometer can measure proper acceleration as a vector quantity and can be used to sense orientation, coordinate acceleration, vibration, and shock of the reference golf club 250.

The sensor components 262 may also include a three-axis gyroscope. The gyroscope is primarily used to measure and maintain orientation of the reference golf club 250 throughout a motion of the reference golf club 250. The three-axis gyroscope also measures angular momentum.

The sensor components 262 may further include a three-axis magnetometer. The magnetometer is used to let the user 202 set a target line for the motion of the reference golf club 250. This is important because each user, including the user 202, has a variation in how they address the golf ball and in their natural degree of slice or hook. Thus, at address, the user 202 chooses a target line, and the actual swing can be compared to that target line for analysis. It should be noted that other devices and/or features may be utilized by the sensor 252 to accomplish the same accounting for variations and orientation as provided by the magnetometer, such as the gyroscope mentioned above.

Each of the sensor components 262 described above may function similarly to the accelerometer, gyroscope, and magnetometer described in U.S. Pat. No. 8,696,482, hereby incorporated by reference. All of the data collected by the sensor components 262 may be stored in the sensor data 256a. In addition, each of the sensor components 262 may collect the sensor data 256a based on the sensor settings 258a stored in the sensor memory 254, as will be discussed in further detail below.

The sensor memory 254 includes the sensor data 256a. The sensor data 256a includes all of the data collected by the sensor components 262 of the sensor 252 before, during, and after motion of the reference golf club 250, such as after a full or partial swing of the reference golf club 250. For example, and without limitation, the sensor data 256a, and/or parameters derived from the sensor data 256a, may include the velocity of any location on the reference golf club 250, including at the sensor 252 location during the motion of the reference golf club 250, the top of the backswing location measured by the point where the reference golf club 250 reverses direction, the location of the reference golf club 150 at address, the torque, the calculated launch direction and velocity of a golf ball struck by the reference golf club 250 based on the impact data calculated by a golf club attached sensor or a golf ball attached sensor, the angle of attack of the golf club head, the club face loft and lie angles measured at address and at impact, the deviation from the address swing plane throughout the swing of the reference golf club 250, the point of release of the wrist of the user 202 during the downswing, the swing tempo/club head velocity at all points throughout the swing, and the shaft deflection based on the reference golf club 250 specifications included in the sensor settings 258a and the calculated torque. In addition, any data measured from the sensors as outlined in U.S. Pat. No. 8,696,482, are hereby incorporated by reference.

The sensor memory 254 further includes the sensor settings 258a. The sensor settings 258a includes data relating to the reference golf club 250 such as the model identification of the golf club or any component thereof, club length, the shaft length, the shaft flex profile, the club type, the volume of the club head, the loft of the club head, the location of the sensor 252 on the golf club, and other data necessary to enable the sensor 252 to capture the sensor data 256a accurately. The sensor settings in some implementations are stored within the sensor at the factory. In some implementations, such information may input by a user or otherwise subsequent to manufacture. In some embodiments, the sensor is provided such setting information by engagement with an electronically readable identification element associated with the reference club, e.g. a barcode, RFID chip, electronically engageable port, or the like. The sensor settings 258a factor into the sensor data 256a directly. For example, in an implementation where the sensor 152 is attached to the shaft of the reference golf club 250, the location of the sensor 252, the length of the shaft, and the club head properties of the reference golf club 250 factor directly into a calculation of other locations of the golf club head at address because the information is used to extrapolate the sensor 252 measurements from the sensor's actual location in space to another location on the club head.

In such an example, the sensor 252 may be configured to enable projection of a 3D vector onto the geometric center of the club face, for example, from a sensor attachment location remote from the geometric center (e.g. a location on the shaft) and determine and record the orientation, velocity, and location data of a 3D vector throughout a swing of the reference golf club 250. In order to determine the location of the geometric center of the face of the club head, the sensor 252 utilizes the sensor settings 258a including the sensor 252 location on the reference golf club 250, the length of the shaft, the orientation of the club head with respect to the sensor 252, and other necessary sensor settings 258a.

In some implementations, the sensor settings 258a may be generic such that any reference golf club 250 can be used to calculate the sensor data 256a. However, more accurate results are captured when the sensor settings 258a include the data of the actual reference golf club 250 being used in capturing the sensor data 256a.

In addition, the sensor settings 258a may include data relating to the user 202 such as the height, age, weight, gender, or golf handicap of the user 202. As such, the sensor settings 258a relating to the user 202 may also be factored into the calculation of the sensor data 256a.

In an implementation where the sensor 252 is located within a golf ball, such as golf ball 103 of FIG. 1, the sensor settings 258 may include the material properties, aerodynamic properties, mass, size, shape, and other information pertaining to the golf ball.

In addition, the computing device 210 and/or the server 270 may transmit additional or updated sensor settings 258a to the sensor 252. The additional or updated sensor settings 258a may include the user data 235 and the additional data 234. For example, the sensor settings 258a may be dynamically updated for each user 202 and location of use of the reference golf club 250, in order to record more accurate and real-time data. As discussed above, the sensor settings 258a are utilized in generating the sensor data 256a, so as the sensor settings 258a are updated, so too is the sensor data 256a.

The system 200 includes the computing device 210 configured to communicate with the sensor 252 and the server 270 over the network 290. The computing device 210 may include a computer, a mobile device, a tablet computer, a wearable device including processing capabilities such as a smart watch, or any other device capable of receiving and/or analyzing data received from the sensor 252.

The computing device 210 includes the device memory 214 and the device processor 211. The device processor 211 is configured to execute computer-readable instructions that are stored in the device memory 214. The instructions may be, for instance, instructions for receiving, transmitting, or analyzing sensor data 256a/256b. The device processor 211 may access the device memory 214 by way of a system bus, for example. The computing device 210 also includes a communication interface 212 configured to allow external devices, such as the server 270 and the sensor 252, to communicate with the computing device 210 and also allow the computing device 210 to communicate with the external devices over the network 290. For example, in some implementations, the computing device 210 may receive data and or instructions for execution by the device processor 211 from an external device.

Various functions of the device memory 214 may be implemented in hardware, software, or any combination thereof. If implemented in software, the functions may be stored as one or more instructions or code and transmitted over a computer-readable medium. A computer-readable storage media may include any available storage media that can be accessed by a computer, and more specifically by a processor, such as the device processor 211. By way of example, and without limitation, computer-readable storage media can comprise RAM, ROM, EEPROM, CD-ROM, or other optical disk storage, magnetic disk storage or other magnetic storage devices, or any other medium that can be used to carry or store desired program code in the form of instructions or data structures that can be accessed by a computer, e.g., device processor 211. In some implementations, the computing device 210 may use a flash memory to store the data and instructions.

The computing device 210 further includes input interface 213. Input interface 213 may include a keyboard, a mouse, a microphone, a display, a joystick, a game pad, a satellite disk, a scanner, or other input devices. These and other input devices are often connected to the device processor 211 through a serial port interface that is coupled to the system bus, but may be connected by other interfaces, such as a parallel port, game port, or universal serial bus (USB), for example.

The computing device 210 further includes a display 238. The display 238 may be a monitor or other type of display device also connected to a system bus via an interface, such as a video adapter. The display 238 may include a plasma, light emitting diode (LED), organic LED, liquid crystal display (LCD), or other suitable display technology. In some implementations, such as where the computing device 210 is a mobile device or a tablet computer, the display 238 may be a touch screen device capable of receiving inputs from a user, such as user 202, via the display 238. In such an implementation, the display 238 also functions as a component of the input interface 213.

The display 238 is configured to display the displayable information of the software application 220b, which may include the data 224, the skill value 237, and any information output from the recommendation engine 225, including recommended golf clubs, shafts, and balls. As such, the software application 220b is configured to transmit the displayable information to the display 238 for visualization and interaction by a user of the computing device 210.

The computing device 210 further includes the software application 220b. The software application 220b is configured to analyze data received from the sensor in order to determine the skill value 237 utilizing the algorithm 236 and to determine the recommended golf clubs 228, shafts 231, and balls 233 utilizing the recommendation engine 225. The software application 220b may be configured to provide feedback about the swing of the user 202, such as by providing the user 202 with a skill value 237 or displaying the swing path 257b and features of the swing path 257b of the user 202 on the display 238 for the user 202 to visualize and interpret. In addition, the software application 220b may be configured to provide a recommended golf club, shaft, or ball from the database 226 based on the analyzed data 224 received from the sensor 252. The software application 220b may be an application designed for a mobile device, a tablet, a computer, or a wearable device, for example, or the software application 220b may be accessed using a web browser on the computing device 210.

In implementations where the software application 220b is accessed using a web browser, the recommendation engine 225 may be stored externally to the computing device 210, such as on the server 270, and accessed by the computing device 210 over the network 290. In implementations where the software application 220b is an application designed for a mobile device, a tablet, or a computer, the software application 220b may include all of the information, algorithms, etc. necessary for the software application 220b to function, thus eliminating the need for the server 270. However, some implementations may utilize both the server 270 and the computing device 210 when operating the software application 220b, whether the software application 220b is accessed via a web browser or configured as an application for a mobile device, a tablet, or a computer, for example.

The software application 220b includes the data 224. It should be noted that the sensor data 256b and the sensor settings 258b correspond respectively to sensor data 256a and sensor settings 258a of sensor 252. Software application 220b is configured to receive the sensor data 256b and the sensor settings 256b from sensor 252 over the network 290, such as a Bluetooth™ network, for example.

The software application 220b is configured to analyze the data 224. For example, after the computing device 210 receives the sensor data 256b from the sensor 252, the software application 220b analyzes the sensor data 256b to determine the swing path 257b of the reference golf club 250 during a swing by the user 202. The sensor data 256b may include three-axis orientation, three-axis velocity, three-axis acceleration, and three-axis location of the club head of the reference golf club 250 during the swing, and after analyzing the sensor data 256b, the software application 220b models a three-dimensional (3D) swing path 257b. The 3D swing path 257b may be again analyzed in determining a length ratio, for example, where the length ratio may be, for example, the distance a location on the club head travels during a backswing as compared to the distance the location on the club head travels during a downswing. In some implementations, the 3D swing path 257b may also be displayed on the display 238 and configured for manipulation by a user of the computing device 210. The swing path 257b will be described in greater detail below.

The data 224 also includes the sensor settings 258b. The software application 220b is also configured to utilize the sensor settings 258b in analyzing the data 224. Although the sensor 252 may utilize the sensor settings 258b in calculating the sensor data 256a, as discussed above, the software application 220b may also utilize the sensor settings 258b in further analyzing of the data 224.

The data 224 further includes the swing parameters 223. The swing parameters 223 include a plurality of different parameters of the swing of the reference golf club 250, and/or characteristics of a motion of the reference golf club 250, based on the sensor data 256b received from the sensor 252. The swing parameters 223 are utilized in generating the algorithm 236 and ultimately the skill value 237, which is utilized by the recommendation engine 225.

As used herein, the term "release" is defined as the release of the wrists by the user 202 during the downswing of the reference golf club 250 in order to position the club face for impact. For practical purposes herein, release is assumed to occur at a point in time during the downswing (i.e., the release point) when the longitudinal axis of the shaft of the reference golf club 250 is substantially parallel with the ground plane, herein referred to as the ¾ point in the swing.

As used herein, the term "swing path" is defined as the path created by a location on the reference golf club 250 during a motion of the reference golf club 250, such as a swing of the reference golf club 250. For example, the swing path 257 may be the path created by the club head of the reference golf club 250 during a full swing. In such an example, the club head creates a 3D path of the backswing and the downswing, where the path includes the orientation, velocity, and position of the club head throughout the full swing. This may be accomplished by recording the orientation, velocity, and location data of a 3D vector having a projected location on the geometric center of the face of the club head, for example. Although the sensor 252 may be mounted on the shaft, in the grip, etc., the sensor 252 utilizes the sensor settings 258a to determine the location of the geometric center of the face of the club head of the reference golf club 250 and records the sensor data 256a from that location. Each of plural locations on the reference golf club 250 may correspond respectively to each of plural swing paths. Of course, location data may be projected onto other locations of the golf club, e.g., the golf club center of gravity, the golf club head center of gravity, or the golf club head geometric center. However, projection onto the geometric center of the face of the club head is preferred as it is indicative of the location of impact with a golf a ball.

It should be noted that FIGS. 5A-5E are incorporated below into the description of the swing parameters 223. FIGS. 5A-5E illustrate various representations of the swing parameters 223 and each include the swing path 596, the backswing segment 597, the downswing segment 598, the golf ball 503, the ground plane 502, and the reference golf club 550. It should be noted that the reference golf club 550 corresponds respectively to the reference golf club 250 of FIGS. 2A-2B.

The swing parameters 223 include "distance to impact." As used herein, distance to impact is defined as the distance of a location on the reference golf club 550, e.g. the striking face, from its corresponding location when the golf club is in the original address position during the downswing and measured at the position of the golf club when at the release point. FIG. 5A illustrates one representation of the distance to impact, and includes the reference golf club 550 at the release point, i.e., the ¾ point of the swing path 596, which occurs when the longitudinal axis of the reference golf club 550 is parallel with the ground plane 502 during the downswing segment 598. As illustrated in FIG. 5A, the distance to impact may be defined as the distance D1, measured from the location on the reference golf club 550 at the original address position 504 to the location on the reference golf club 550 at the release point 505. In some implementations, the distance D1 may be measured as the straight line distance in 3D space between the release point 505 and the original address position 504. In other implementations, the distance D1 may be measured as the straight line distance as projected onto a two-dimensional (2D) plane. The swing path 596 may be considered from various vantage points, and thus, it is contemplated that the distance to impact measurement may be projected onto one of several virtual planes. For example, the distance to impact may be measured based on the swing path 596 projected onto a vertical 2D plane extending perpendicular to the face of the club head of the reference golf club 550 when the club head is at address.

However, the distance to impact measurement is not intended to be limited to a straight line measurement, but may, in some implementations, be measured as the distance along the downswing segment 598 of the swing path 596 in 3D space or as projected onto a 2D plane, similar to the 2D planes described above.

The swing parameters 223 further include "release ratio." As used herein, the release ratio is a comparison between the amount of time from the beginning of the downswing to the release point compared to amount of time during the downswing from the release point to impact.

The swing parameters 223 also include "swing path width." As used herein, the swing path width is defined as the maximum distance between the backswing and the downswing segments of the swing path measured perpendicular to the arc of the downswing. Similar parameters may be considered having interchangeable practical use with swing path width as may be described below in more detail. For example, a lateral swing path width may be considered to have similar informational value as swing path width, but measured as the maximum distance between the backswing and the downswing in a virtual horizontal plane (i.e., parallel to the virtual ground plane), limited to the region of the swing in which points on the downswing are laterally spaced from corresponding points on the backswing.

Another similar parameter that, for practical purposes herein, may be considered to be interchangeably functional with swing path width is a projected swing path width. Projected swing path width as used herein denotes a distance measured based on the swing path projection onto a two-dimensional (2D) plane. The swing path may be considered from various vantage points, and thus, it is contemplated that a swing path width may be projected onto one of several virtual planes. For example, with reference to the position of the golf club when oriented in an initial address position, the swing path width may be measured based on the swing path projected onto a vertical 2D plane extending parallel to the face of the club head of the reference golf club 250 when the club head is at address. FIG. 5B illustrates one representation of the projected swing path width measurement. The swing path 596 in FIG. 5B is projected onto the plane of the paper, where the plane of the paper extends parallel to the club face of the reference golf club 550 when the reference golf club 550 is at the original address position. FIG. 5B includes the reference golf club 550 at the ¼ point of the swing path 596 on the backswing segment 597 as reference golf club 550a, and further includes the reference golf club 550 at the ¾ point of the swing path 596 on the downswing segment 598 as reference golf club 550b. As such, the distance D2 is a measurement of the distance between a location on the reference golf club 550, such as at the geometric center of the face, at the ¼ point and at the ¾ point of the swing. It should be noted that the ¼ point of the swing is the point in the backswing when the longitudinal axis of the reference golf club 250 is parallel with ground plane 502.

However, in some embodiments, the swing path width may be measured based on the maximum distance between the backswing and the downswing segments of the swing path in 3D space, where each distance measurement is taken along a straight line extending perpendicular to the arc of the downswing).

The swing parameters 223 also include "swing path area." As used herein, the swing path area is defined as the area between the backswing and the downswing segments of the swing path. The swing path area may be measured based on the swing path projection onto a two-dimensional (2D) plane. For example, the swing path area may be measured based on the swing path projected onto a 2D vertical plane extending perpendicular to the face of the club head of the reference golf club 550 when the club head is oriented in an initial address position. Referring to FIG. 5C, FIG. 5C illustrates one representation of the swing path area measurement. As such, the swing path area is the area between the backswing segment 597 and the downswing segment 598 of the swing path 596, denoted by solid parallel lines in FIG. 5C.

The swing parameters 223 include "angular velocities." As used herein, the angular velocities is defined as the maximum angular velocity during the downswing of the reference golf club 550 about an axis extending parallel to the ground plane and through the club face of the reference golf club 550 when the club head is at the original address position.

The swing parameters 223 further include "maximum velocity." As used herein, the maximum velocity (of a location on a reference golf club, e.g., golf club 550) is defined as the maximum velocity achieved by a designated location on the reference golf club 550 during the swing. Maximum velocity may be considered, for example, at the geometric center of the face of the club head. For all practical purposes herein, it is contemplated that various recitations of "maximum velocity" below may also be considered substitutable with similar measurement values. For example, such recitations of "maximum velocity," as may be variously provided below in association with swing analysis systems, processes and/or apparatuses, are contemplated to be substitutable with a swing velocity value taken at a controlled, predetermined absolute location relative to a reference point (e.g., the geometric center of the striking face of the club head in an initial address position), relative to one or more locations regarding the geometric extent of the swing, and/or at an absolute or relative predetermined point in time during the swing.

Figure 5E:
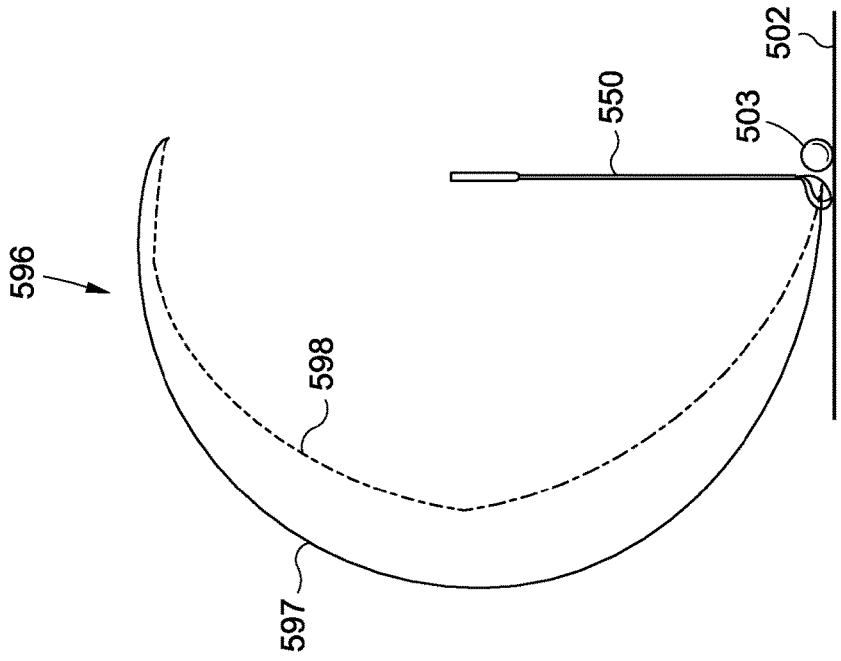
Figure 5D:
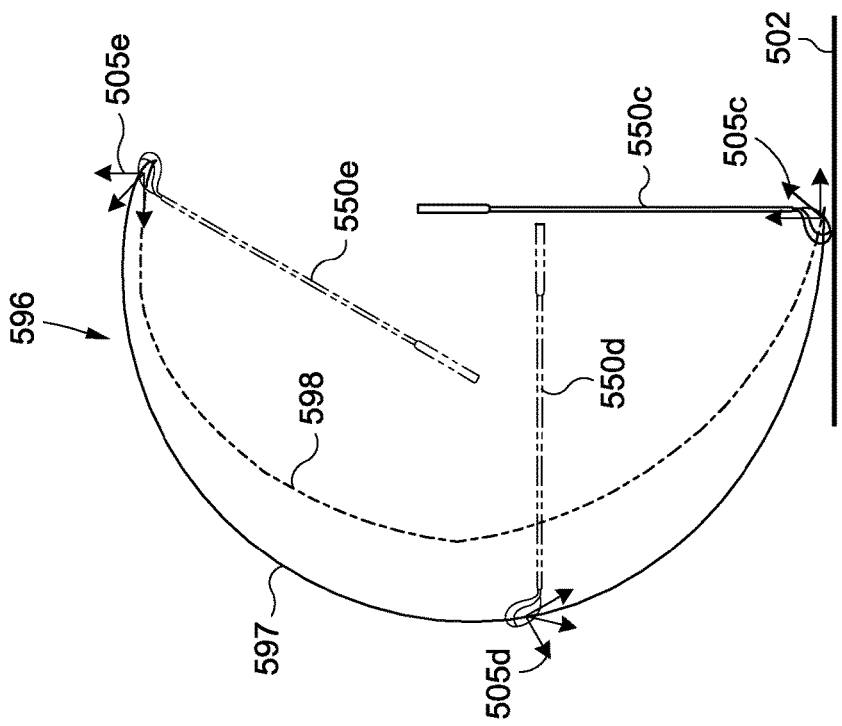

Referring to FIG. 5D, FIG. 5D illustrates a non-limiting representation of various points in the swing where velocity may be measured in order to determine a maximum velocity. For example, swing velocity values (associated with a specified location on a reference golf club, e.g., golf club 550) may be taken at a location on the reference golf club 550 at the ¼ (illustrated by reference golf club 550d), ½ (represented by reference golf club 550e), ¾, or impact (represented by reference golf club 550c) points of the swing. FIG. 5D further includes three-axis velocity vectors 505c, 505d, and 505e corresponding respectively to the reference golf club 550c, 550d, and 550e at various points in the swing. The three-axis velocity vectors are included to illustrate that the velocity of the location on the reference golf club 550 is measured about three axes at all points during the swing, and the magnitude of the velocity vectors at every point during the swing may be calculated to find the maximum velocity of the swing. In other embodiments, swing velocity values (associated with a specified location on the reference golf club 550) may be taken at a point in time relative to the swing duration, such as the time of impact.

The swing parameters 223 also include "velocity ratio." As used herein, the velocity ratio (of a specified spatial point along a specified swing path of a specified location on a reference golf club, e.g., golf club 250) utilizes the maximum velocity defined above, and is defined as the percentage of the maximum velocity of a measured swing velocity of the specified location on the reference golf club 250 at the specified point in the specified swing path. For example, the velocity ratio may be considered for the velocity of the center of the face of the club head at impact compared to the maximum velocity of the center of the face of the club head during a swing by the user 202. In another example, the velocity ratio may be considered for the velocity of the center of the face of the club head at the ¾ swing point compared to the maximum velocity of the center of the face of the club head during a swing by the user 202.

The swing parameters 223 may include one or more comparisons between length aspects of the swing path. FIG. 5E illustrates a representation of a swing path. In some embodiments, the swing parameters 223 include a comparison between the respective lengths of at least two different directional components of the swing path 596 created by a location on the reference golf club 550 during the swing of the reference golf club 550. For example, and more specifically, the comparison may be between the length of the backswing segment 597 created by the geometric center of the face of the club head as compared to the length of the downswing segment 598 created by the center of face of the club head during the swing of the reference golf club 550. In addition or alternatively, the comparisons may include a comparison between the lengths of two different portions of the backswing segment 597 or two different portions of the downswing segment 598. In yet another example, the comparison may be between the length of a portion of the backswing segment 597 compared to a length of a portion of the downswing segment 598, and vice versa. Comparisons may also be measured based on the swing path projection onto a two-dimensional (2D) plane extending with respect to a reference coordinate. For example, a length comparison may be measured based on the swing path 596 projected onto a 2D vertical plane extending perpendicular to the face of the club head of the reference golf club 550 when the club head is oriented at an initial address position. In some implementations, length comparisons may also include a comparison of at least two different directional segments of the swing path 596 as measured in 3D space based on the distance traveled by a location on the club face of the reference golf club 550, for example.

Although a plurality of parameters are outlined above with respect to the swing parameters 223, the listed parameters are not intended to be limiting. For example, any number of other parameters may be utilized based on the sensor data 256b received from the sensor 252, including any parameters derived from the orientation, velocity, acceleration, and location of the reference golf club 250 during the swing by the user 202.

Referring back to FIG. 2, the data 224 further includes additional data 234. The additional data 234 may include data relating to the location of the computing device 210 and/or the sensor 252. The location may be determined utilizing a Global Positioning System (GPS) or another suitable location device. The additional data 234 may further include weather information pertaining to the location, including climate conditions, which may factor into the sensor data 256b, the sensor settings 258b, and/or the swing parameters 223. The additional data 234 may be factored in to the swing parameters 223, to account for atmospheric pressure, turf conditions, moisture, and other information that may be utilized manually, or dynamically, to update the sensor settings 258a/258b, in order to more accurately record the sensor data 256a/256b, or to provide more data to the recommendation engine.

The data 224 includes the user data 235. The user data 235 may include the location, age, gender, race, nationality, height, weight, arm length, torso length, body type, wrist to ground length, and other user data 235 relating to the user 202 of the reference golf club 250. The user data 235 may further include preferences of the user 202, such as the desired or undesired golf club types. The user data 235 may include historical data of the user 202 such as the golf clubs currently or previously used by the user 202, the handicap of the user 202, and/or the frequency and location of play of the user 202. Such data may also include previously measured, calculated, and/or outputted information provided to a user using the same or a similar analysis process or apparatus. In some implementations, the reference golf club 250 may be customized by the user 202, or may have different characteristics than those included in the sensor settings 258b. In such an implementation, the user data 235 may further include customization information of the user 202, such as adjusted characteristics of the reference golf club 250, including length, loft, and lie characteristics. The user data 235 may be utilized manually, or dynamically, to update the sensor settings 258a/258b, in order to more accurately record the sensor data 256a/256b, or to provide more data to the recommendation engine.

The software application 220b also includes the algorithm 236. The algorithm is configured to receive input values, which may include at least one of the swing parameters 223, and to output the skill value 237. The algorithm 236 may be generated in a plurality of different ways, and may include any number of the swing parameters 223 as part of its formula. It should be noted that the algorithm 236 may include multiple different algorithms. For example, separate algorithms may be utilized for outputting the skill value 237 utilized by the recommendation engine 225 for generating a club head recommendation, a ball recommendation, or a shaft recommendation. However, in some implementations, a single algorithm may output the single skill value 237 that is utilized in making a recommendation of club head, ball, and shaft.

As an example, in one implementation, the algorithm 236 may only include one or more of the swing parameters 223 which are used to determine the skill value 237. In such an implementation, the swing parameters 223 may be normalized so as to output the skill value 237 such that the skill value 237 matches one of the golf club skill values 227.

As another example, in some implementations, in order to determine which of the swing parameters 223 to utilize in generating the algorithm 236, a least squares regression analysis may be performed. First, a plurality of users having varying known handicaps and known skill levels can take swings with the reference golf club 250. For each swing, each of the swing parameters 223 can be calculated based on the sensor data 256b. The resulting combinations of known skill level and parameter value are plotted. For each swing parameter 223, a linear regression analysis is performed by generating a best-fit straight line through the set of data points, i.e., in such a way as to make the sum of squared residuals ($r^2$), or, in other words, the vertical distances between the data points and the straight line, as small as possible. As a result of the simple linear regression, an $r^2$ value is determined for each of the swing parameters 223 and compared. The larger the $r^2$ value of the swing parameters 223, the less deviation the data points have from the straight line, and thus the more consistent and telling the swing parameters 223 are believed to be of skill level.

Based on the above process, it was believed that one or more swing parameters, either alone or in combination with each other, may serve as acceptable candidates for predicting a skill level for a golfer using a swing analysis device or process. In addition to considering $r^2$ values, other factors were believed to be relevant to this determination. For example, the nature and extent of outliers were considered as were the nature of an erroneous recommendation. For example, consideration was afforded to understanding the reasoning behind an erroneous recommendation, the constitution of erroneous recommendations and any psychological effect that such erroneous recommendation may have on a potential user. Ultimately, based on at least some of the above factors, it was determined that a comparison between an aspect of the backswing to a corresponding aspect of the downswing of a recorded swing path stood out as a preferable means for predicting golfer skill level. More specifically, the comparison includes a length ratio being a ratio between the length of the backswing segment of the swing path and the length of the downswing segment of the swing path. In some such embodiments, optionally, such lengths are determined as lengths measured of the projection of the swing path in a virtual plane. In some embodiments, a determination of skill level is based at least in part on maximum velocity (as defined above), which also had been considered to have a high $r^2$ value. In some such embodiments, maximum velocity is solely used to calculate skill level. Although the length ratio and the maximum velocity were determined to be preferable, it should be noted that any of the swing parameters 223 may be used in generating the algorithm 236.

Once the swing parameters 223 for use in the algorithm 236 are determined, they may be normalized such that when the swing parameters 223 are input into the algorithm 236, the skill value 237 output by the algorithm always falls within the range of one of the golf club skill values 227 within the database 226 of the recommendation engine 225 such that a golf club, a shaft, and/or a golf ball can be recommended. The swing parameters 223 may be normalized based on generic values, such as normalizing to 1, or may be normalized based on the results of testing. In an implementation where testing is conducted, a maximum average value may be used to normalize the swing parameters 223.

For example, if the swing parameter being tested is the maximum velocity, and one hundred users take swings with the reference golf club 250, the ten highest maximum velocities may be averaged, and yield a number such as 115 mph. As such, the swing parameter of maximum velocity may be normalized to 115 mph, such that the values for the maximum velocity are input into the algorithm 236 as a percentage of 115 mph. In such an implementation, if the user 202 has a maximum velocity of 115 mph, the value 1 would be input into the algorithm 236. If the user 202 has a maximum velocity of 57.5 mph, the value 0.5 would be the input into the algorithm 236, and so on.

For another example, if the swing parameter being tested is the length ratio, where the length ratio in this example is the 3D distance a location on the club head of the reference golf club travels during the backswing compared to the 3D distance the location travels during the downswing, then after the one hundred users take swings with the reference golf club 250, the ten highest length ratios may average to 1.5, meaning the backswing length is 1.5 times longer than the downswing length. In such an example, the length ratio may be normalized to 1.5.

In other examples, various curve-fitting operations are developed to associate quantitative swing data with skill level. For example, normalization may be associated with a skill level value by curve-fitting to a Gaussian distribution or other normal distribution. However, in some cases, particularly where the boundaries between skill levels cannot be accurately drawn from a single swing parameter, relationships may be developed for controlling how multiple swing parameters may interplay to correspond with a recommended skill level. In such cases, values may be determined, e.g., empirically, by which to add, subtract, multiply, and/or divide the swing parameters 223 values by, such that when the swing parameters 223 are used in the algorithm 236, the skill values 237 output fall within a certain range that matches up with the range of values of the golf club skill values 227 in the database 226. The values by which to add, subtract, multiply, and/or divide may come from testing, such as that discussed above, or may be based on analysis of different values and their effect on the algorithm 236 outputs. The software application 220b may utilize values from the swings of a plurality of users of the reference golf club 250 to determine equations that output results, e.g., skill values 237, within a specific range, or at least where a specified percentage of input values would output results within a specific range. In some embodiments, curve-fitting modules are stored such that the processor may automatically develop swing parameter to skill level relationships based on input swing information from a group of users. In some cases, relationships are develop in such a manner and adaptable based on new input. For example, information regarding a club that a user actually purchased in combination with some information regarding his or her swing may be stored and used to either verify the integrity of the recommendation engine and/or to automatically adjust how the recommendation engine correlates swing data with skill level. In some cases, the recommendation engine determines a skill level value based on swing data, whereby the determination is based entirely on feedback information regarding correspondences between swing data and actually purchased golf clubs. In this manner, the processor may be adapted to continuously run e.g., perform $r^2$ best-fit analysis based on a continually updating stream of data, and continuously adjust its skill level recommendation module based on such $r^2$ best-fit analysis.

For one example of algorithm 236, the swing parameters 223 used were the length ratio and the maximum velocity, where the length ratio in this example was the 3D distance a location on the club head of the reference golf club travels during the backswing compared to the 3D distance the location travels during the downswing. The skill values 237 desired were in the range of 2-9. During testing, a predetermined set of the highest maximum velocities recorded averaged to about 115 mph, and from this number, with the goal of normalizing maximum velocity to be useful in predicting skill values 237 in the range of 2-9, the following equation (1) was determined:

$$\text{Max Velocity Final} = (\text{Maximum Velocity} - 70 \text{ mph})/5 \text{ mph} \quad (1);$$

If the Max Velocity Final was greater than 9, or less than 2, the Max Velocity Final was rounded to 9 or 2, respectively. Also during testing, the highest length ratios recorded averaged to about 1.5, and from this number, with the goal of normalizing the length ratio to be useful in predicting skill values 237 in the range of 2-9, the following equation (2) was determined:

$$\text{Length Ratio Final} = (\text{Length Ratio} - 1.05) \times 20 \quad (2);$$

If the Length Ratio Final was greater than 9, or less than 2, the Length Ratio Final was rounded to 9 or 2, respectively. After calculating Max Velocity Final and Length Ratio Final, the following equation (3) was utilized to calculate the skill value 237:

$$\text{Skill Value} = (\text{Max Velocity Final} + \text{Length Ratio Final})/2 \quad (3);$$

As such, the skill value 237 output by the algorithm falls within a range of 2-9, which was designed to match the golf club skill values 227 assigned to the golf clubs 228, shafts 231, and the balls 233 in the database 226.

The software application 220b further includes the recommendation engine 225. The recommendation engine 225 is configured to utilize the data 224 and/or the skill value 237 to determine recommended golf clubs 228, shafts 231, and/or balls 233. Once the recommendation engine 225 has determined the recommended golf clubs 228, shafts 231, and/or balls 233, the recommendation engine can send the information pertaining to the recommendations to the display 238 for visualization and interaction by a user of the computing device 210.

It should be noted that the recommendation engine 225 is illustrated with dashed lines to indicate that the recommendation engine 225, or certain components thereof, may not be stored on the device memory 214, but may be stored externally, such as on the server 270. For example, in implementations where the database 226 includes a large quantity of golf clubs 228, shafts 231, and balls 233, it may be desirable to store that information externally to the computing device 210 based on data storage capacity requirements of the computing device 210.

The recommendation engine 225 includes the database 226. The database 226 is configured to store the golf club skill values 227 and information regarding the identification and aspects of the golf clubs 228, the shafts 231, and the balls 233. The recommendation engine 225 is updated dynamically as new products are introduced, old products are phased out, and current products become sold out or otherwise unavailable. For example, if the recommendation engine 225 recommends golf club A from the golf clubs 228 having a 10.5 degree loft, but determines that the 10.5 degree loft is sold out, the recommendation engine 225 will recommend another loft. In addition, as new data is collected using the sensor 252, and other sensors in communication with the network 290, the golf club skill values 227 may be updated for each of the golf clubs 228, the shafts 231, and the balls 233.

The database 226 includes the golf club skill values 227. The golf club skill values 227 are values that are assigned to each of the golf clubs 228, the shafts 231, and the balls 233. The golf club skill values 227 assigned to each of the golf clubs 228, the shafts 231, and the balls 233 may be a single value, or a range of values. For example, golf club A of the golf clubs 228 may include a golf club skill value of 5, such that when the skill value 237 is 5, golf club A is recommended. In another example, golf club A may include the golf club skill values 227 ranging from 4.7 to 5.3, such that when the skill value 237 is 5, golf club A is recommended.

The golf club skill values 227 are not intended to be limited to the golf clubs 228, and may also apply to the shafts 231 and the balls 233. For example, the balls 233 and the shafts 231 may also have associated golf club skill values 227 based on the golf club skill values 227 of the golf clubs 228 described above. In such an example, the shafts 231 and the balls 233 may be assigned the golf club skill values 227 corresponding to the golf club skill values 227 assigned to the golf clubs 228 that match the skill values 237 based on the algorithm 236. In this manner, golf ball and/or shaft recommendations may be determined and outputted/displayed using the same skill level generating module that is used for golf club head recommendation.

However, in other implementations, separate algorithms may be used for determining skill values for the balls 233 and the shafts 231. In such an implementation, the algorithm for the balls 233 may calculate a ball skill value and the algorithm for the shafts 231 may calculate a shaft skill value. The algorithms for calculating the ball and shaft skill values may utilize the swing parameters 223 and the sensor data 256b. For example, the ball skill value may be based on the impact conditions as measured by the sensor 252, where the sensor 252 may be a ball sensor similar to that of ball sensor 104 in FIG. 1. As another example, a ball skill level recommendation may be made by parameters detected from sensor 152a. However, in some embodiments, such parameters either: (a) differ in one or more respects from those parameters used in generating a club head skill level; (b) are the same parameters used in generating a club head level but differently weighted or otherwise considered in generating a skill level value; or (c) some combination of (a) and (b). For example, it may be contemplated that certain swing attributes are more critically determinative of skill level for balls than for club head. For example, for golf balls, it may be considered that velocity at impact should carry greater weight in ball selection than length ratio, and thus, velocity at impact may also carry greater weight for generating golf ball skill value.

The golf clubs 228 may include models 229 and properties 230. In addition to the golf clubs 228 having corresponding golf club skill values 227, the individual models 229 of the golf clubs 228 may also have corresponding skill values. For example, the golf clubs 228 may include a family of drivers, and each member of the family of drivers may correspond to one of the models 229. As such, each of the models 229 may include its own golf club skill values 227.

In addition, the golf clubs 228, including the models 229, include the properties 230. The properties 230 include the loft, lie, club face angles, and other properties of the golf clubs 228. The loft, lie, club face angle, weight insert mass(es), and other properties of the golf clubs 228 may be recommended utilizing the golf club skill values 227, or may be recommended based on other data 224. For example, once one of the golf club 228 having one of the models 229 has been recommended by the recommendation engine 225, the recommendation engine 225 may utilize the swing parameters 223, the sensor data 256, and/or other data 224 to determine the properties 230 of the golf club 228. In such an example, the recommendation engine 225 may recommend model A from the models 229 based on the golf club skill values 227. After recommending model A, the recommendation engine 225 may utilize the angle of attack and velocity information at impact from the data 224 to determine that a prescribed loft, e.g., a 10.5 degree loft, is recommended.

As used herein, the term "attack angle" is defined as an angle at which a geometric center of a face of a club head is moving at a point of impact with a golf ball or virtual golf ball measured with respect to, and in a plane perpendicular to, the ground plane. The positive angle of attack is when the club head strikes the ball moving upwards, and negative is when the club head is moving downwards when striking the ball.

As used herein, the term "impact loft" of a club face of a reference golf club 250 denotes an angle measured at impact between a virtual ground plane and a line extending normal to the face of the club head of the reference golf club 250 at the geometric center of the face and projected onto a virtual vertical plane perpendicular to the general striking face plane considered when the club head is oriented in an initial address position.

An actual loft recommendation may be determined utilizing the attack angle, impact loft, and velocity data of the club head of the reference golf club 250 generated by the sensor data 256b. In some embodiments, the recommendation engine 225 may utilize a plurality of attack angle data points and maximum velocity data points to determine an ideal impact loft of the club head for each possible combination of attack angle and maximum velocity. In addition, impact loft may be compared to the actual designated club head loft value from the sensor settings 258b to determine a delta loft.

The delta loft is the difference between the designated club head loft value as optionally stored in sensor settings 256b and the impact loft. The delta loft is then subtracted from the ideal impact loft generated by the recommendation engine 225 for the measured attack angle and velocity of the swing of the reference golf club 250 to output a recommended actual loft. The recommendation engine 225 then utilizes the static loft value to find golf clubs 228 from the database 226 having designated lofts closest to the static loft.

For example, assume the recommendation engine 225 determines, based on the skill value 237, that golf club A is the recommended golf club for user 202. The recommendation engine 225 may then utilize the recommended actual loft output, which may be 9.7, in this example, to determine the proper loft designation of golf club A to recommend to the user 202. If golf club A is offered in designated lofts of 8.5, 9.5, and 10.5, based on the properties 230 in the database 226, the recommendation engine 225 would recommend a loft of 9.5 which is closest to the static loft 9.7 output by the loft determination done by the software application 220b.

Although the above example describes the recommendation engine 225 determining the recommended actual loft independent of the recommended golf club for the user 202, this example is not intended to be limiting. In another example, the recommendation engine 225 may recommend golf club A to the user 202 based on the skill value 237, for example, and then utilize a plurality of attack angles and velocities to determine the ideal impact loft of golf club A for each possible combination of attack angle and velocity, utilizing the properties 230 of golf club A, specifically. At this point, the remaining steps of the process for determining the loft recommendation would continue as discussed above.

The recommendation engine 225 may utilize the swing parameters 223 directly to recommend the golf clubs 228, the shafts 231, and the balls 233. For example, the database 226 may include recommended values for the swing parameters 223 for each of the golf clubs 228, the shafts 231, and the balls 233. As a result, when the recommendation engine 225 receives the swing parameters 223 after a swing of the reference golf club 250 by the user 202, the recommendation engine 225 can recommend any number of the golf clubs 228, the shafts 231, and the balls 233, including models 229 and properties 230 of the golf clubs 228, and properties 232 of the shafts 231.

The recommendation engine 225 may utilize the additional data 234 to determine recommended golf clubs 228, shafts 231, and balls 233. For example, if the additional data 234 includes location data, the recommendation engine 225 may only recommend the golf clubs 228, the shafts 231, and the balls 233 that are available in that location. As such, if the user 202 lives in the United States, for example, the recommendation engine 225 will only recommend items from the database 226 that are available in the United States. As another example, if the additional data 234 includes turf conditions, the recommendation engine 225 may only recommend balls 233 that perform well on those turf conditions. Such determination of turf conditions may be a function of geographic location to be determined using GPS or other transmitted location data.

The recommendation engine 225 may utilize the user data 235 to determine recommended golf clubs 228, shafts 231, and balls 233. For example, if the user data 235 includes the height and gender of the user 202, the recommendation engine 235 may only recommend the golf clubs 228, the shafts 231, and the balls 233 recommended for a user of that gender and height. For another example, if the user 202 specifies that they prefer golf clubs with draw or fade correction or golf clubs with no weight inserts, the recommendation engine 225 may only recommend the golf clubs 228 capable of draw and fade correction and/or no weight inserts.

The database 226 further includes the shafts 231 including the properties 232. The shafts 231 may include any number of different shafts, and each of the shafts 231 may be designed for a certain club type, or may be designed for multiple club types. The properties 232 of the shafts 231 include the flex, the flex profile, the length, the materials, adjustability characteristics, and other properties necessary for the recommendation engine 225 to recommend the shafts 231. The flex includes, for example, X (extra stiff), S (stiff), R (regular), A (amateur) and W (women's). The flex profile may alternatively, or in addition, include flex profiles based on other conventional flex profile coding system, e.g., a conventional profile coding system that represents shaft stiffness at plural locations about the length of the shaft. For example, shaft recommendations may include the shaft profiling convention described in U.S. Pat. No. 8,337,336 (incorporated by reference herein in its entirety), particularly the convention described at page 3, line 20 to page 5, line 48. One example of a correlation between swing parameters 223 and recommended shaft properties 232 includes if the user 202 has a high maximum velocity value as one of the swing parameters 223, the recommendation engine 225 may recommend one of the shafts 231 having a stiffer flex, such as S or X flex. In addition, the recommendation engine 225 may take into account other of the swing parameters 223, or skill values 237, to determine a proper flex profile for the shaft of the user 202, such as a flex profile of "7457" (with regard, e.g., to the shaft selection convention described at page 3, line 20 to page 5, line 48 of U.S. Pat. No. 8,337,336 described above), where the butt end and the tip end have more stiffness than the central sections of the shaft.

The recommendation engine 225 may also utilize the sensor data 256b, calculated utilizing the sensor settings 258b which include the flex profile of the reference golf club 250, to determine the deflection of the shaft of the reference golf club 250 during the swing by the user 202. The deflection information can then also become a factor in recommending one of the shafts 231 having properties 232 suitable for the user 202. For example, if the deflection of the shaft is beyond a certain threshold value, the recommendation engine 225 may recommend one of the shafts 231 having a stiffer flex profile. On the other hand, if there is a small amount of deflection in the shaft of the reference golf club 250 during the swing the user 202, the recommendation engine 225 may recommend one of the shafts 231 having a less stiff flex profile, such as a shaft having the flex profile "3242" (with regard, e.g., to the shaft selection convention described at page 3, line 20 to page 5, line 48 of U.S. Pat. No. 8,337,336 described above), for example.

The database 226 further includes the balls 233. In some implementations, the balls 233 may include the golf club skill values 227 and be recommended based on the match to the skill value 237 e.g., as described above. In some implementations, the balls 233 may be recommended based off of the sensor data 256b, including calculated ball spin, ball flight path, and ball flight distance based on the impact conditions of the club head of the reference golf club 250, for example. As an example, if the ball spin is calculated to have a high side spin, the recommendation engine 250 may recommend one of the balls 233 designed for reduced spin. In addition, any number of the swing parameters 223 may be utilized in recommending the balls 233. For example, if the user 202 has a high maximum velocity during the swing, the recommendation engine 225 may recommend one of the balls 233 designed for high swing speeds.

Figure 2B:
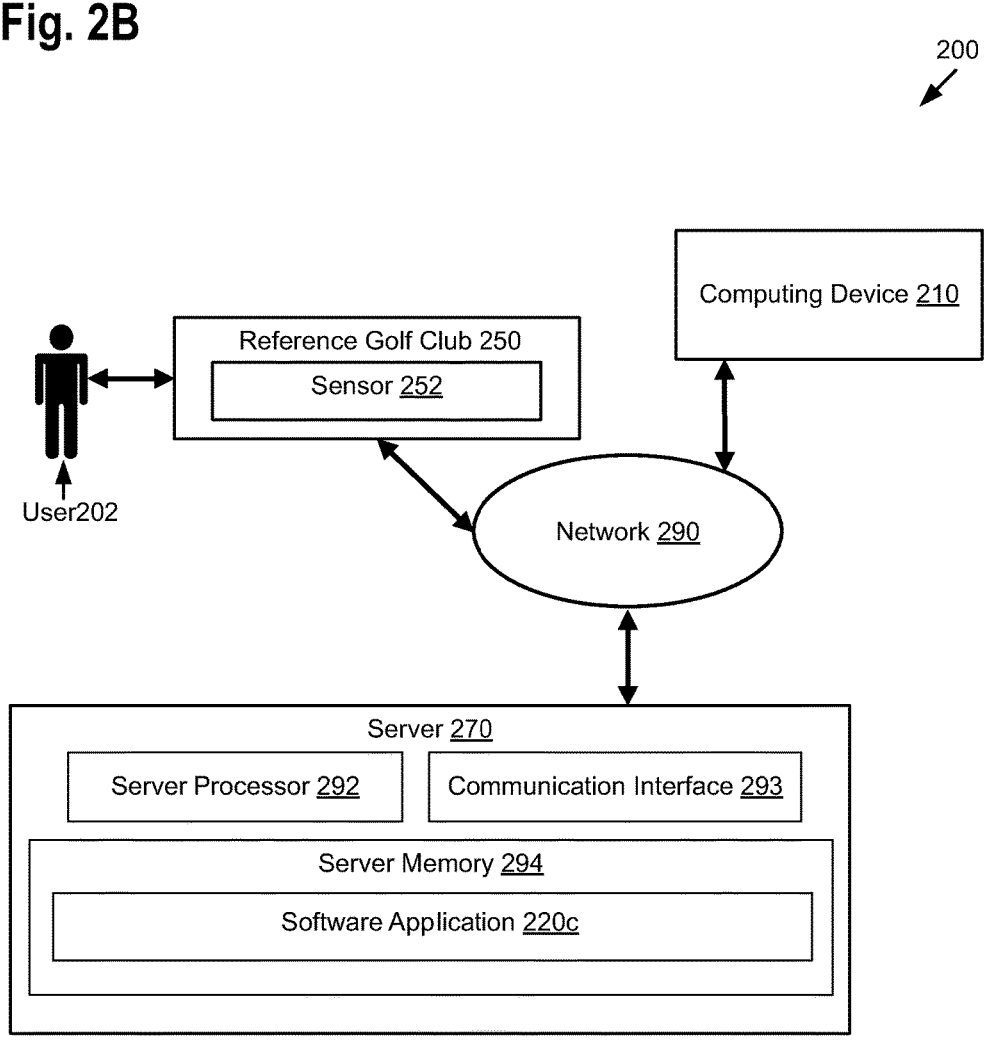
FIG. 2B is another illustration of the system of FIG. 2A for analyzing a sporting apparatus, according to one implementation of the present disclosure.

Now referring to FIG. 2B, FIG. 2B is another illustration of the system of FIG. 2A for analyzing a sporting apparatus, according to one implementation of the present disclosure. The system 200 of FIG. 2B includes the user 202, the reference golf club 250 including the sensor 252, the network 290, the computing device 210, and the server 270. The server 270 includes server processor 292, communication interface 293, and server memory 294. The server memory 294 includes the software application 220c. It should be noted that the user 202, the reference golf club 250, the sensor 252, the computing device 210, the network 290, the server 270, and the software application 220c of FIG. 2B correspond respectively to the user 202, the reference golf club 250, the sensor 252, the computing device 210, the network 290, the server 270, and the software application 220b of FIG. 2A.

The server 270 includes the server memory 294 and the server processor 292. The server processor 292 is configured to execute computer-readable instructions that are stored in the server memory 294. The instructions may be, for instance, instructions for receiving, transmitting, or analyzing data from the sensor 252 and/or the computing device 210. The server processor 292 may access the server memory 294 by way of a system bus, for example. Various functions of the server memory 294 may be implemented similarly to that of the device memory 214 described above.

The server 270 also includes a communication interface 293 configured to allow external devices, such as the computing device 210 and the sensor 252, to communicate with the server 270 and also allow the server 270 to communicate with the external devices over the network 290. For example, in some implementations, the server 270 may receive data and or instructions for execution by the server processor 292 from an external device.

The server memory 294 includes the software application 220c. The software application 220c may include some or all of the features of the software application 220b stored on the computing device 210. For example, in some implementations, the server 270 may only store the recommendation engine 225 on the server memory 294 and receive the data 224 and the algorithm 236 from the computing device 210. In such an example, the server 270 may determine the recommended golf clubs, shafts, and balls and transmit that data back to the computing device 210 using the network 290. However, in other implementations, the server 270 may store all of the data 224, the recommendation engine 225, and the algorithm 236 such that the server 270 can perform calculations independently of the computing device 210. In such an implementation, the server 270 may use the data 224, the algorithm 236, and the recommendation engine 225 to determine recommended clubs, shafts, and balls and transmit the information to the computing device 210, thereby freeing up processing and storage capabilities for the computing device 210.

It should be noted that although only one server 270 is illustrated in FIGS. 2A and 2B, any number of servers 270 may be implemented. For example, each of the servers 270 may be operated by a different manufacturer, such that each server 270 utilizes a recommendation engine 225 to recommend golf clubs 228, shafts 231, and balls 233 from each respective manufacturer. In such an implementation, the computing device 210 can display a number of different recommended golf clubs, shafts, and balls from a variety of different manufacturers. In addition to each recommendation engine 225 on each server 270 filtering through the database 226 to determine recommendations, an additional recommendation engine 225 on the computing device 210 may filter through the results from each of the manufacturers to output the golf clubs 228, shafts 231, and balls 233 from manufacturers that the user 202 prefers based on the user data 235, for example. Additionally, multiple manufacturers may share servers, or one server 270 may be operated for all manufacturers together.

It should be noted that the software application discussed with reference to FIGS. 3A-3C corresponds to the software application 220b and 220c of FIGS. 2A and 2B.

Figure 3A:
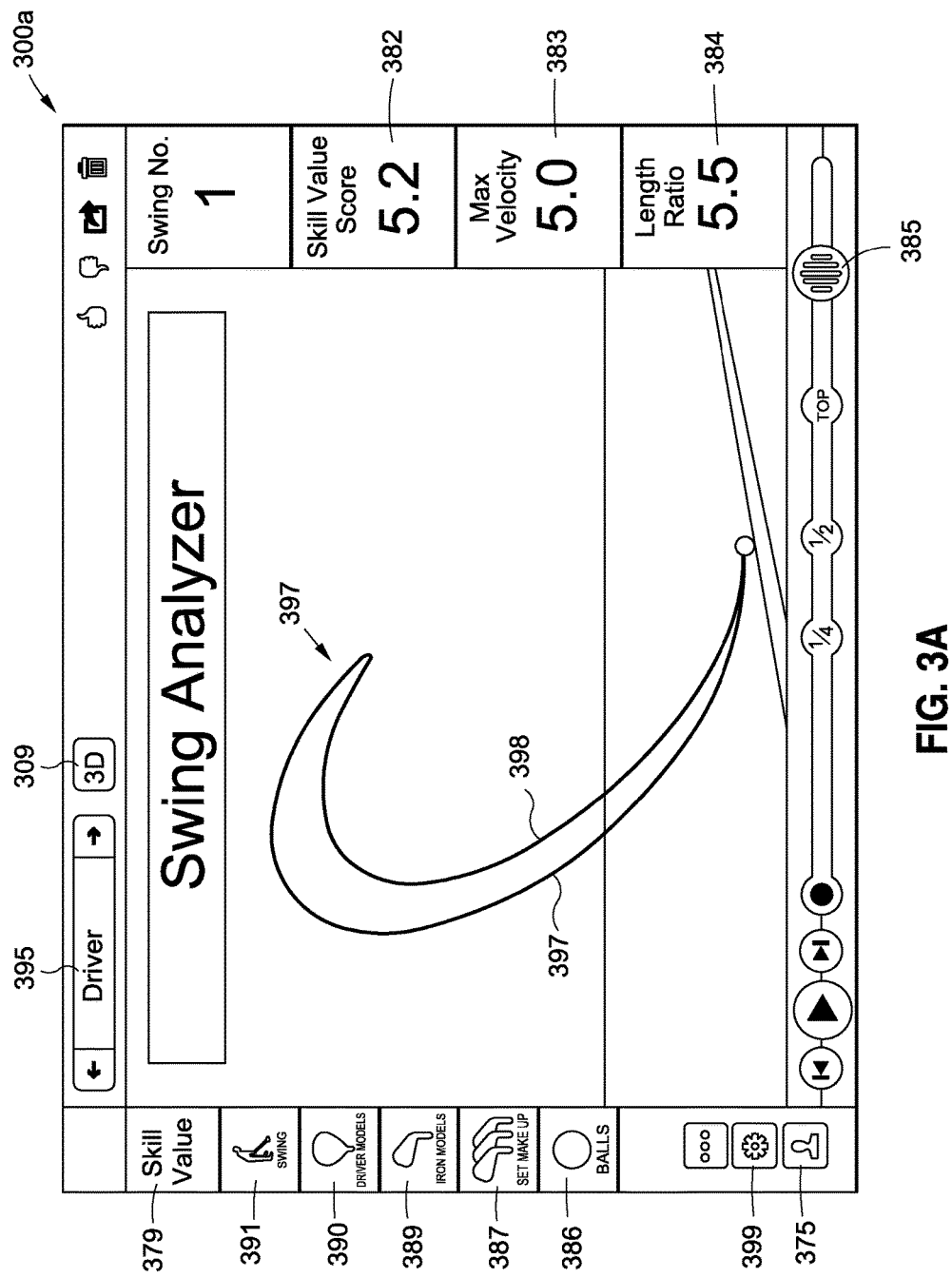
FIG. 3A is an illustration of a display of a software application for analyzing a sporting apparatus, according to one implementation of the present disclosure.

Now referring to FIG. 3A, FIG. 3A illustrates a display of a software application for analyzing a sporting apparatus, according to one implementation of the present disclosure. Display 300a of FIG. 3A includes reference golf club 395, swing value tab 379, swing analyzer tab 391, driver models tab 390, iron models tab 389, set make up tab 387, ball tab 386, settings tab 399, user tab 375, skill value display 382, max velocity display 383, length ratio display 384, swing path 396, backswing segment 397, downswing segment 398, swing view 309, and swing view playback 385.

Figure 3B:
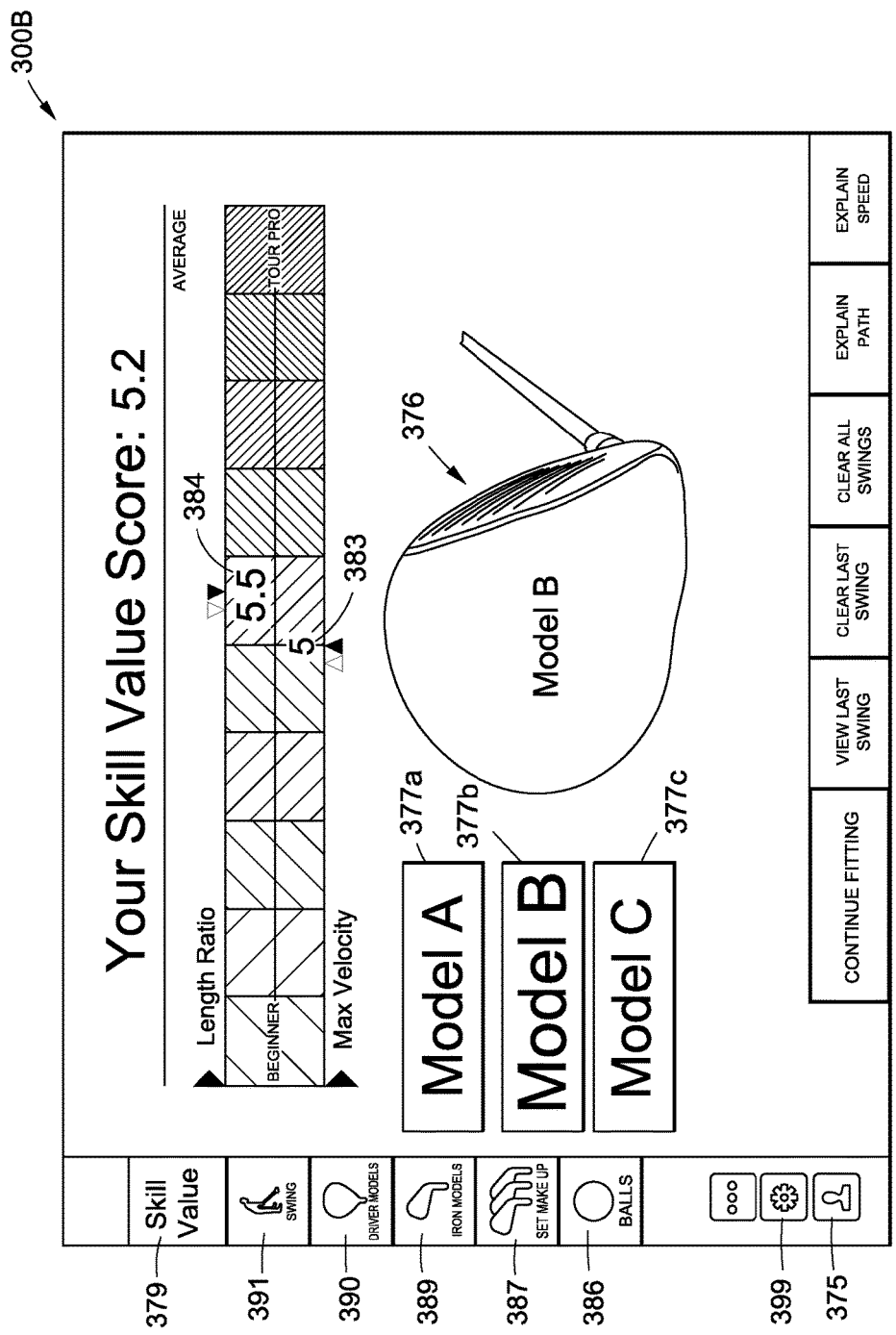
FIG. 3B is an illustration of another display of the software application for analyzing a sporting apparatus of FIG. 3A, according to one implementation of the present disclosure.

The swing value tab 379, when selected, is configured to open another display of the software application, which is described in further detail with respect to FIG. 3B.

Figure 3C:
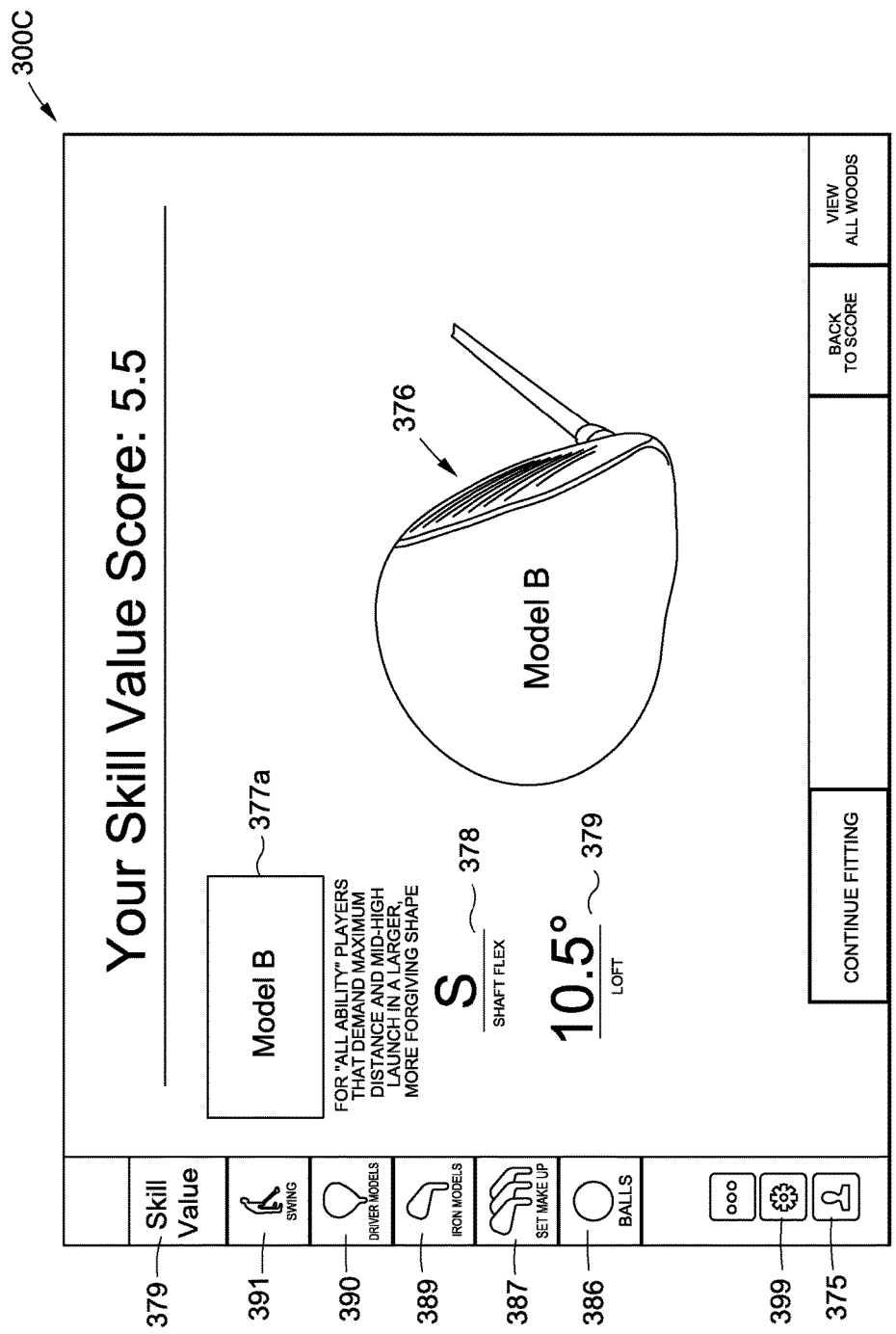
FIG. 3C is an illustration of another display of the software application for analyzing a sporting apparatus of FIGS. 3A and 3B, according to one implementation of the present disclosure.

The driver models tab 390, when selected, is configured to open another display of the software application, which is described in further detail with respect to FIG. 3C.

The iron models tab 389, when selected, is configured to open another display for the software application for viewing recommended iron models. For example, where the reference golf club 395 is an iron type golf club, the software application may recommend the iron type golf clubs based on the sensor data collected and the swing parameters. In examples where the reference golf club 395 selected is not an iron type golf club, but a driver, for example, the iron models tab 389 may still provide recommendations of iron type golf clubs based on the swing parameters of the swing with the driver. For example, if the software application recommends a driver for game-improvement type player having skill values ranging from 1-3, the iron type golf clubs recommended on the display of the iron models tab 389 may include irons that also include skill values ranging from 1-3.

The set make up tab 387, when selected, is configured to open another display of the software application for viewing recommended set make ups. Similar to the iron models tab 389, described above, the software application may recommend not only the golf club determined based on the reference golf club 395 type, but also the additional clubs necessary to complete, or at least partially complete, a set of golf clubs. For example, if the reference golf club 395 is a driver, and the software application recommends a driver for skill values ranging from 1-3, the software application may also generate a set of fairway woods, irons, hybrids, and wedges designed for players of skill values ranging from 1-3, such as the golf clubs 228 having the golf club skill values 227 ranging from 1-3 of FIG. 2A. In addition to recommending the different club types, the software application may be configured to determine and recommend a set make-up. For example, the application may be configured to recommend how many wedges the user should have. Also, as an example, the application may be configured to recommend how many hybrids and/or irons are necessary for players having the skill values and swing parameters of the user swinging the reference golf club. For example, players with very low skill values, around 1-3, may benefit from having hybrids in place of their 3, 4, 5, and 6 irons because hybrids are characteristically easier to hit, while players with higher skill values, around 3-5, may only require a 3 and 4 hybrid, because players of those skill values may be more capable of hitting a 5 or 6 iron.

The ball tab 386, when selected, is configured to open another display of the software application for viewing recommended balls. The software application may display each of the balls available with a description of the balls, allowing the player to choose based on descriptions. However, the software application may be configured to utilize the impact conditions measured by a club attached sensor, such as the sensor 152a of FIG. 1, or impact conditions measured by a golf ball sensor, such sensor 104 of FIG. 1, to recommend a ball. For example, if the impact conditions show high values of side spin, the software application may recommend a ball that produces less spin. For another example, the software application may utilize the skill value 237 to determine balls that are recommended for players having a skill value 237 of the user.

The setting tab 399, when selected, is configured to open another display of the software application for viewing and/or altering the settings of the software application, the computing device, and the sensor. For example, the user of the software application may be able to change the settings of the reference golf club 395 and/or the sensor attached to the reference golf club, such as the sensor settings 258a of the sensor 252 of FIG. 2A. In addition, the location, time, date, battery, brightness, and other settings of the software application and the computing device operating the software application may be viewed and/or changed in the setting tab 399. The location, for example, may change the recommended golf clubs in the driver models tab 390, the iron models tab 389, and the set make up tab 387, in addition to the balls in the ball tab 386 to only display golf clubs and balls that are available in that location.

The user tab 375, when selected, is configured to open another display of the software application for viewing and/or changing the user data. The user data, such as the user data 235 of FIG. 2A, can be changed and viewed in the user tab 375. For example, if the user of the software application updates the data of the user of the reference golf club, such as the reference golf club 250 in FIG. 2A, the updated user data can be transmitted to the sensor, such as sensor 252 of FIG. 2A, in order to calculate more accurate results.

The swing analyzer tab 391, when clicked, is configured to open the display 300a on the computing device, such as the computing device 110 of FIG. 1.

The display 300a includes the reference golf club 395 that includes the type of golf club having the attached sensor, such as reference golf club 250 and sensor 252 of FIG. 2A. The software application may include any number of available options for the reference golf club 395, and each of the reference golf clubs 395 may include any number of characteristics. For example, when a user of the software application selects the reference golf club 395, the software application may transmit the characteristics of the reference golf club 395 to the sensor attached to the reference golf club, such as one of sensors 152 attached to the reference golf club 150 in FIG. 1.

The display 300a further includes the skill value display 382. The skill value display 382 is configured to display the skill value, such as the skill value 237 based on the algorithm 236 of FIG. 2A. The skill value may be normalized to fall within a specified range, as described in more detail above with respect to FIG. 2A. In the illustrated display 300a of FIG. 3A, the skill value display 382 includes the skill value of 5.2 which is a rounded average of the max velocity and length ratio displayed in the max velocity display 383 and the length ratio display 384, respectively.

The display 300a further includes the max velocity display 383. The max velocity display 383 is configured to display the maximum velocity, such as the maximum velocity from the swing parameters 223 of FIG. 2A. The maximum velocity may be normalized to fall within a specified range, as described in more detail above with respect to FIG. 2A.

The display 300a further includes the length ratio display 384. The length ratio display 384 is configured to display the length ratio, such as the length ratio from the swing parameters 223 of FIG. 2A. The length ratio may be normalized to fall within a specified range, as described in more detail above with respect to FIG. 2A.

It should be noted that although the display 300a includes only the max velocity display 383 and the length ratio display 384, any other swing parameters and/or data, such as the swing parameters 223 and data 224 of FIG. 2A, may also be included in the display 300a. For example, in some implementations, the swing parameters and data used in calculating the skill value may be the swing parameters and data displayed on display 300a.

The display 300a includes the swing path 396 having the backswing segment 397 and the downswing segment 398. The swing path 396 is generated from tracking the orientation, location, and velocity in 2D and/or 3D space of a location on the reference golf club throughout a swing of the reference golf club, such as reference golf club 150 of FIG. 1. Visualizing the swing path 396 on the display allows the user of the software application to analyze the swing, and also provides visual feedback to the user of the reference golf club as to the swing parameter values, including the length ratio and the maximum velocity, for example, and ultimately feedback on the calculated skill value.

The display 300a also includes the swing view 309 that when selected is configured to allow the user of the software application to view the swing path 396 in different orientations and dimensions. For example, the swing view 309 may allow the user to select between 2D and 3D, viewing of the swing path 396, or to change the orientation to a rear, side, top, or front view of the swing path 396.

The swing path 396 may also be illustrated in an environment that provides depth and clarity for analyzing the swing path 396, such as in a clean room type environment, as illustrated in FIG. 3A. The depth and clarity of the environment allow the user to more noticeably identify the characteristics of the swing path 396, especially when displayed in 3D space, on the display.

The software application is further enabled to allow a user to manually manipulate the swing path 396 by zooming in, zooming out, and rotating the swing path 396, for example, using an input device such as a mouse or keyboard, or by using finger gestures on a touch-screen display of the device operating the software application, such as the display 238 of the computing device 210 in FIG. 2A.

The display 300a further includes the swing view playback 385 configured to allow user control of playback, fast-forward, rewind, stop, and pause the swing path 396 on the display. For example, in FIG. 3A the entire swing path 396 is shown, including the backswing segment 397 and the downswing segment 398, but the swing view playback 385 is configured to display the swing path 396 as it was/is created during a swing of the reference golf club, such as reference golf club 150 of FIG. 1. The swing view playback 385 includes selectable locations in the swing path 396 including the ¼ swing location, the ½ swing location, and the top swing location, for example. The ¼ swing location is when the reference golf club shafts longitudinal axis is substantially parallel to the ground plane during the backswing segment 397, the ½ swing location is when the reference golf club shafts longitudinal axis is substantially perpendicular to the ground plane, and the top swing location is when the reference golf club reverses direction. As such, the user of the software application is able to quickly navigate to the specific locations within the swing path 396 for analysis.

Now referring to FIG. 3B, FIG. 3B is an illustration of another display of the software application for analyzing a sporting apparatus of FIG. 3A, according to one implementation of the present disclosure. The display 300b of FIG. 3B includes the swing value tab 379, swing analyzer tab 391, driver models tab 390, iron models tab 389, set make up tab 387, ball tab 386, settings tab 399, user tab 375, skill value display 382, max velocity display 383, length ratio display 384, model 377a, model 377b, model 377c (hereinafter referred to collectively as models 377), and recommended golf club 376. It should be noted that the swing value tab 379, swing analyzer tab 391, driver models tab 390, iron models tab 389, set make up tab 387, ball tab 386, settings tab 399, user tab 375, skill value display 382, max velocity display 383, length ratio display 384 of FIG. 3B correspond respectively to the swing value tab 379, swing analyzer tab 391, driver models tab 390, iron models tab 389, set make up tab 387, ball tab 386, settings tab 399, user tab 375, skill value display 382, max velocity display 383, length ratio display 384 of FIG. 3A.

The length ratio display 384 and the max velocity display 383 of display 300b include a scale, where each of the triangles represent the length ratio and the maximum velocity for each swing, and the displayed value is an average of the all of the swings. The scale may range between the normalized values of the length ratio and the maximum velocity, from 0-10, as an example. In one example, a first swing may be taken with the reference golf club, such as reference golf club 150 of FIG. 1, and the length ratio and the maximum velocity may be calculated and normalized and then indicated in display 300b with a white triangle. A second swing may then be taken, with the maximum velocity and the length ratio indicated in display 300b by black triangles, and so on. In some implementations, the most recent swing may be indicated by a black triangle, while all prior swings are indicated by triangles of like color, such as white, for example. For each additional swing, the average value of the length ratio and the maximum velocity is dynamically updated in the length ratio display 384 and the max velocity display 383, respectively. As a result, the skill value display 382 reflects the updated average of the maximum velocity and the length ratio after each swing.

The display 300b further includes the models 377. The models 377 may include all available models for the user of the reference golf club, or may include only the models having golf club skill values closest to the skill value calculated by a swing of the reference golf club by the user. For example, if the user is looking to find a recommended driver, and they are right handed, and located in the United States, the software application may only display the models 377 that are available to the user and display the models, such as illustrated in display 300b. Once the user takes a swing, or a plurality of swings, with the reference golf club, the skill value updates and the model with the closest golf club skill value to the updated skill value is recommended. The recommendation may be displayed by, for example, bolding, highlighting, italicizing, enlarging, or otherwise alternating the appearance of the name of the model in comparison to the other listed models, and/or by displaying the model on the screen. The display 300b provides an example illustrating the model 377b as bolded and enlarged relative to models 377a, 377c, and by displaying the recommended golf club 376.

After a number of swings, the skill value may update, and the recommended golf club 376 may change, and the change is then reflected on the display similar to above. For example, the skill value after two swings may be 5.3, and the model 377b may be recommended based on its golf club skill value range being between 5 and 6.9. After fifteen swings, the skill value may change to 3.9, and as a result the model 377a may be recommended based on its golf club skill value of 3 to 4.9. As such, the display 300b is configured to dynamically update with each new swing of the reference golf club.

Now referring to FIG. 3C, FIG. 3C is an illustration of another display of the software application for analyzing a sporting apparatus of FIGS. 3A and 3B, according to one implementation of the present disclosure. The display 300c of FIG. 3C includes the swing value tab 379, swing analyzer tab 391, driver models tab 390, iron models tab 389, set make up tab 387, ball tab 386, settings tab 399, user tab 375, skill value display 382, model 377b, recommended golf club 376, shaft properties 378, and club head properties 379. It should be noted that the swing value tab 379, swing analyzer tab 391, driver models tab 390, iron models tab 389, set make up tab 387, ball tab 386, settings tab 399, user tab 375, skill value display 382, recommended golf club 376, and model 377b of FIG. 3C. correspond respectively to the swing value tab 379, swing analyzer tab 391, driver models tab 390, iron models tab 389, set make up tab 387, ball tab 386, settings tab 399, user tab 375, skill value display 382, recommended golf club 376, and model 377b of FIG. 3B.

Once the model 377b and the recommended golf club 376 are determined, the shaft properties 378 and the club head properties 379 can further be displayed. The shaft properties 378 may include the flex, the flex profile, the length, the balance point, the kickpoint, the model, or the manufacturer. The shaft properties 378 are recommended based on the swing parameters, the sensor data, and the recommended golf club, as discussed in further detail above with respect to the FIG. 2A.

The club head properties 379 may include the loft, lie, weight adjustability, and/or other features relating to the club head of the recommended golf club 376.

It should be noted with respect to FIG. 3B and FIG. 3C that more than one golf club and/or model, shaft, ball, shaft properties 378, and/or club head properties 379 can be recommended.

Figure 4:
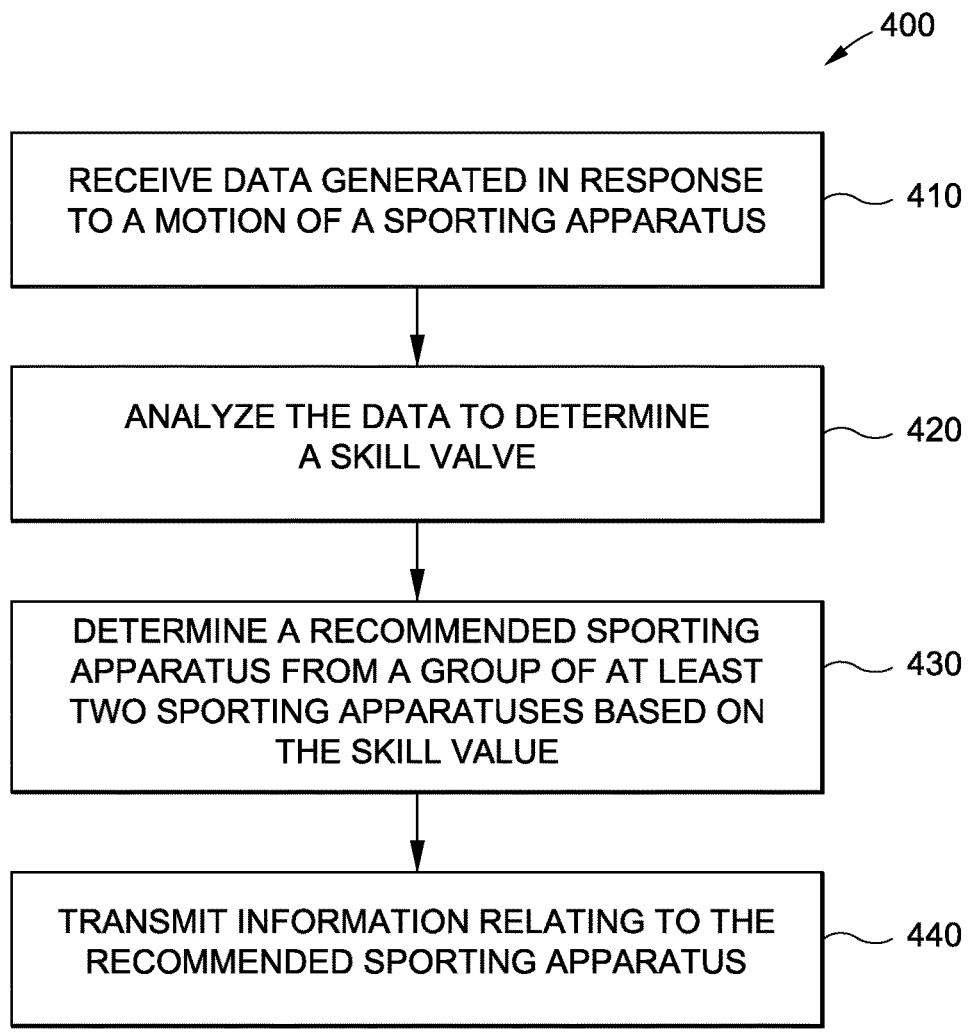
FIG. 4 is a flowchart diagram illustrating a method for use by systems and apparatus of the present disclosure.

Now referring to FIG. 4, FIG. 4 is a flowchart diagram illustrating a method for use by systems and apparatus of the present disclosure. The approach and technique indicated by flowchart 400 are sufficient to describe at least one implementation of the present disclosure, however, other implementations of the disclosure may utilize approaches and techniques different from those shown in flowchart 400. Furthermore, while flowchart 400 is described with respect to FIGS. 2A-2B, the disclosed inventive concepts are not intended to be limited by specific features shown and described with respect to FIG. 3. Furthermore, with respect to the method illustrated in FIG. 4, it is noted that certain details and features have been left out of flowchart 400 in order not to obscure the discussion of inventive features in the present application.

Flowchart 400 will be described with respect to two implementations, implementation A and B. This is in no way to provide limitation, but only to explain two possible implementations of the present disclosure. Implementation A does not include the use of the server 270, while implementation B includes the use of the server 270.

Flowchart 400 (at 410) includes receiving data generated in response to a motion of a sporting apparatus. For example, with regards to implementation A, the computing device 210 may receive the sensor data 256a and the sensor settings 258a from the sensor 252 across the network 290, such as a Bluetooth™ network, in response to a swing of the reference golf club 250.

For another example, with regards to implementation B, the server 270 may receive the sensor data 256a and the sensor settings 258a from the sensor 252 over the network 290, such as a WAN, in response to a swing of the reference golf club 250. However, in some implementations, the computing device 210 may first receive the sensor data 256a and the sensor settings 258a from the sensor 252 over the network 290, such as a ZigBee™ network, and then transmit the sensor data 256b and the sensor settings 258b to the server 270 over the network 290, such as a WAN.

Referring again to flowchart 400, flowchart 400 (at 420) includes analyzing the data to determine a skill value. For example, with regard to implementation A, the software application 220b may first utilize the sensor data 256b and the sensor settings 258b to calculate the swing parameters 223, such as length ratio and maximum velocity. The software application 220b may then be configured to normalize the computed swing parameters 223, and input the swing parameters 223 into the algorithm 236 to determine the skill value 237.

Another example, with regard to implementation B, includes the software application 220c on the server 270 first utilizing the sensor data 256b and the sensor settings 258b to calculate the swing parameters 223, such as length ratio and maximum velocity. The software application 220b may then be configured to normalize the computed swing parameters 223, and input the swing parameters 223 into the algorithm 236 to determine the skill value 237. However, in some implementations, the computing device 210 may first utilize the sensor data 256b and the sensor settings 258b to calculate the swing parameters 223 and ultimately the skill value 237, and then transmit the skill value 237 to the server 270 for use in the next step of determining a recommended sporting apparatus.

Flowchart 400 continues (at 430) with determining a recommended sporting apparatus from a group of at least two sporting apparatuses based on the skill value. For example, with regards to implementation A, the recommendation engine 225 may determine at least one of the golf clubs 228, the shafts 231, and the balls 233 from the database 226 based on a match between the skill value 237 and the golf club skill value 227. However, the recommendation engine 225 may utilize any of the skill value 237, the swing parameters 223, or the sensor data 256b to determine the recommended golf clubs 228, shafts 231, and balls 233, in addition to the models 229 and properties 230 of the golf clubs 228, as well as the properties 232 of the shafts 231.

For another example, according to implementation B, the recommendation engine 225 on the server 270 may determine at least one of the golf clubs 228, the shafts 231, and the balls 233 from the database 226 based on a match between the skill value 237 and the golf club skill value 227. However, the recommendation engine 225 may utilize any of the skill value 237, the swing parameters 223, or the sensor data 256b to determine the recommended golf clubs 228, shafts 231, and balls 233, in addition to the models 229 and properties 230 of the golf clubs 228, as well as the properties 232 of the shafts 231. Once the server 270 has determined the recommended golf clubs 228, shafts 231, and balls 233, the recommendation engine 225 on the computing device 210 may further filter the recommendations based on the user data 235 and/or the additional data 235, including location data, for example.

Referring again to flowchart 400, flowchart 400 (at 440) includes transmitting information relating to the recommended sporting apparatus. For example, in regards to implementation A, the computing device 210 may transmit the information relating to the recommended golf club to the display 238 of the computing device 210. The information pertaining to the recommended golf club may include the model and loft, in addition to the shaft model and flex, for example.

For another example, in regards to implementation B, the server 270 may transmit the information pertaining to the recommended golf club over the network 290 to the computing device 210, for rendering on the display 238 of the computing device 210.

The present disclosure describes a system and method for analyzing the swing of a user for determining a recommended sporting apparatus for that user. Modern recommendation engines primarily utilize launch conditions of a ball that are the result of a swing, but do not analyze the swing itself. The launch conditions provided by these modern recommendation engines can only provide limited information about the actual swing of the user, especially because most launch conditions are tested on hard mats at driving ranges or indoor fitting areas, which do not adequately reflect real world impact conditions of the users swing. However, by analyzing the physical swing of the user, utilizing the swing parameters, more information about the skill level of the user is collected in comparison to only testing the launch conditions of the ball because the swing of the user itself remains more consistent throughout varying turf conditions and locations where the swing is recorded. Ultimately, the above described implementations provide a more accurate representation of the skill level of the user, and as a result the system described provides more accurate recommendations of sporting apparatuses.

In describing preferred implementations of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method comprising:
   (a) detecting, using an electronic position sensor, user-specific swing data comprising three-dimensional position data of a location on a reference golf club detected at points of time throughout a test swing of a specific user;
   (b) receiving the swing data using a processor;
   (c) obtaining rules that identify user skill values based on comparisons between first values of a first spatial attribute of a first swing segment and second values of a second spatial attribute of a second swing segment that is different from the first segment, the comparisons identified as correlative of skill value with an acceptable degree of predictiveness;
   (d) identifying, based on at least the user-specific swing data, a first user-specific value corresponding to the first spatial attribute and a second user-specific value corresponding to the second spatial attribute;
   (e) determining a user skill value based on the user-specific first and second values and on the rules obtained in step (c);
   (f) retrieving recommended skill values associated with each of a plurality of golf clubs from a database;
   (g) based on the user skill value and the recommended skill values retrieved in step (f), transmitting a recommendation of at least one of the plurality of golf clubs.

2. The method of claim 1, wherein step (e) further comprises determining the user skill value by applying the second user-specific value to an algorithm generated based on correlations between empirical skill value data and empirical motion characteristic data.

3. A method for analyzing a reference golf club, the method comprising the steps of:
   (a) generating an algorithm based on correlations between empirical skill value data and empirical spatial characteristic data, the algorithm being configured to receive at least one user-specific value and calculate a user skill value;
   (b) receiving, from a sensor device, swing data of a specific user's swing of the reference golf club, the swing data including three-dimensional position data of a location on the reference golf club detected throughout the swing;
   (c) calculating based on at least the three-dimensional position data, a user-specific value representative of a relationship between a first value of a spatial characteristic attributable to a first golf swing portion and second value of the spatial characteristic attributable to a second golf swing portion;
   (d) determining the user skill value from the user-specific value by applying the user-specific value to the algorithm;
   (e) determining that the user skill value corresponds to at least one recommended skill value associated with a recommended golf club from a group of at least two golf clubs; and
   (f) transmitting information relating to the recommended golf club.

4. The method recited in claim 3, wherein:
   step (a) further comprises generating the algorithm based on correlations between the empirical skill value data and empirical motion characteristic data;
   step (b) further comprises calculating a second user specific value representative of a motion characteristic of the second golf swing portion; and
   step (c) further comprises determining the user skill value from the second user-specific value by applying the second user-specific value to the algorithm.

5. The method recited in claim 3, wherein the algorithm is generated using a least squares regression analysis.

6. The method recited in claim 3, wherein step (e) comprises:
   comparing the user skill value to the recommended skill value associated with the at least two golf clubs from the group; and
   outputting, as the recommended golf club, the golf club from the group that has the recommended skill value that most closely matches the user skill value.

7. The method recited in claim 3, wherein step (e) comprises:
   determining at least one of a recommended loft of a club head and a recommended shaft flex of a shaft of the recommended golf club; and
   transmitting the at least one of the recommended loft and the recommended shaft flex along with the information relating to the recommended golf club.

8. A method comprising:
   (a) receiving swing data of a specific user's swing of a reference golf club generated by a sensor device associated with the reference golf club, the swing data including three-dimensional position data of a location on the referenced golf club detected throughout the swing;
   (b) calculating, based on at least the three-dimensional position data, a user-specific value representative of a relationship between a first value of a spatial characteristic attributable to a backswing portion of the swing a second value of the spatial characteristic attributable to the downswing portion of the swing;
   (c) determining a user skill value from the user-specific value by applying the user-specific value to an algorithm, the algorithm generated based on correlations between empirical skill value data and empirical spatial characteristic data;
   (d) retrieving recommended skill values associated with each of a plurality of golf clubs from a database;
   (e) determining at least one of the recommended skill values from the database is similar to the user skill value; and
   (f) transmitting information relating to the at least one of the golf clubs having the recommended skill value similar to the user skill value.

9. The method of claim 8, wherein the spatial characteristic includes a length.

10. The method of claim 8, wherein the algorithm is generated using a least squares regression analysis.

11. The method of claim 8, wherein step (g) further comprises:
   determining at least one of a recommended loft of a club head and a recommended shaft flex of a shaft of the at least one of the golf clubs; and
   transmitting the at least one of the recommended loft and the recommended shaft flex along with the information relating to the at least one of the golf clubs.

12. In a system implementing a reference golf club comprising a shaft, a grip, and a club head, a sensor device attached to at least one of the shaft, the grip, and the club head, and a computing device, a method comprising:
   (a) receiving swing data of a specific user's swing of the reference golf club, the swing data including three-dimensional position data of a location on the reference golf club detected throughout the swing;
   (b) calculating, based on at least the three-dimensional position data, a user-specific value for a length ratio, the length ratio comprising a relationship between a first value for a length of a backswing segment of the swing and a second value for a length of a downswing segment of the swing;
   (c) determining a user skill value from the user-specific value by applying the user-specific value to an algorithm, the algorithm generated based on correlations between empirical skill value data and empirical length ratio data;
   (e) determining a recommended golf club from a group of at least two golf clubs based on the user skill value; and
   (f) transmitting, by the computing device, information relating to the recommended golf club.

13. The method recited in claim 12, wherein the position data is captured by:
   projecting a three-dimensional vector onto the location on the reference golf club; and
   recording at least one of orientation, velocity, and location data of the three-dimensional vector through the swing of the reference golf club.

* * * * *